United States Patent
Hamill et al.

(10) Patent No.: US 11,439,491 B2
(45) Date of Patent: Sep. 13, 2022

(54) SYSTEMS AND METHODS FOR PROTECTING THE CEREBRAL VASCULATURE

(71) Applicant: Claret Medical, Inc., Santa Rosa, CA (US)

(72) Inventors: Whittaker Ian Hamill, Petaluma, CA (US); Shih Hsiung Albert Yuan, Pleasanton, CA (US); Antony J. Fields, San Francisco, CA (US); Cameron Paul Purcell, Santa Rosa, CA (US); Daniel Wayne Fifer, Windsor, CA (US); James Richard Watson, Santa Rosa, CA (US)

(73) Assignee: Claret Medical, Inc., Santa Rosa, CA (US)

( * ) Notice: Subject to any disclaimer, the term of this patent is extended or adjusted under 35 U.S.C. 154(b) by 433 days.

(21) Appl. No.: 16/395,412

(22) Filed: Apr. 26, 2019

(65) Prior Publication Data

US 2019/0328502 A1  Oct. 31, 2019

Related U.S. Application Data

(60) Provisional application No. 62/663,117, filed on Apr. 26, 2018.

(51) Int. Cl.
*A61F 2/01* (2006.01)
(52) U.S. Cl.
CPC ............ *A61F 2/013* (2013.01); *A61F 2/011* (2020.05)
(58) Field of Classification Search
CPC .. A61F 2/01; A61F 2/011; A61F 2/012; A61F 2/013
See application file for complete search history.

(56) References Cited

U.S. PATENT DOCUMENTS 3,472,230 A  10/1969 Fogarty
4,619,246 A  10/1986 Molgaard-Nielsen et al.
(Continued)

FOREIGN PATENT DOCUMENTS

DE  10049812 A1  4/2002
EP  1400257 A2  3/2004
(Continued)

OTHER PUBLICATIONS

Internet Archive Wayback Machine; Fiber Innovative Technology: FIT Capabilities; downloaded from http://web.archive.org/web/20010217040848/http://www.fitfibers.com/capabilities.htm (Archived Feb. 17, 2001; printed on Dec. 12, 2016).
(Continued)

*Primary Examiner* — Melanie R Tyson
(74) *Attorney, Agent, or Firm* — Seager, Tufte & Wickhem LLP

(57) ABSTRACT

Disclosed are methods and devices for isolating all three of the left subclavian, left common carotid and brachiocephalic arteries from embolic debris that might flow through the aortic arch, via a single access point. A system may include an elongate flexible tubular sheath, having a proximal end and a distal end, and an inner member extending through the sheath and moveable relative to the sheath. A left subclavian element may be supported by the inner member. A filter membrane may be configured to isolate the aorta from the brachiocephalic, left common carotid and left subclavian arteries when the left subclavian element is expanded within the left subclavian artery and the sheath is retracted to expose the membrane. The left subclavian element may include a self expandable frame, which may carry a left subclavian filter.

11 Claims, 19 Drawing Sheets

(56) References Cited

U.S. PATENT DOCUMENTS

| | | | |
|---|---|---|---|
| 4,630,609 | A | 12/1986 | Chin |
| 4,650,466 | A | 3/1987 | Luther |
| 4,706,671 | A | 11/1987 | Weinrib |
| 4,723,549 | A | 2/1988 | Wholey et al. |
| 4,873,978 | A | 10/1989 | Ginsburg |
| 5,108,419 | A | 4/1992 | Reger |
| 5,192,286 | A | 3/1993 | Phan et al. |
| 5,200,248 | A | 4/1993 | Thompson et al. |
| 5,329,923 | A | 7/1994 | Lundquist |
| 5,348,545 | A | 9/1994 | Shani et al. |
| 5,381,782 | A | 1/1995 | DeLaRama et al. |
| 5,395,327 | A | 3/1995 | Lundquist et al. |
| 5,613,980 | A | 3/1997 | Chauhan |
| 5,624,430 | A | 4/1997 | Eton et al. |
| 5,662,671 | A | 9/1997 | Barbut et al. |
| 5,680,873 | A | 10/1997 | Berg et al. |
| 5,707,389 | A | 1/1998 | Louw et al. |
| 5,766,151 | A | 6/1998 | Valley et al. |
| 5,779,716 | A | 7/1998 | Cano et al. |
| 5,814,064 | A | 9/1998 | Daniel et al. |
| 5,827,324 | A | 10/1998 | Cassell |
| 5,833,650 | A | 11/1998 | Imran |
| 5,848,964 | A | 12/1998 | Samuels |
| 5,897,529 | A | 4/1999 | Ponzi |
| 5,897,819 | A | 4/1999 | Miyata et al. |
| 5,910,154 | A | 6/1999 | Tsugita et al. |
| 5,910,364 | A | 6/1999 | Miyata et al. |
| 5,911,734 | A | 6/1999 | Tsugita et al. |
| 5,935,139 | A | 8/1999 | Bates |
| 5,980,555 | A | 11/1999 | Barbut et al. |
| 5,989,281 | A | 11/1999 | Barbut et al. |
| 5,993,469 | A | 11/1999 | McKenzie et al. |
| 6,001,118 | A | 12/1999 | Daniel et al. |
| 6,010,522 | A | 1/2000 | Barbut et al. |
| 6,027,520 | A | 2/2000 | Tsugita et al. |
| 6,042,598 | A | 3/2000 | Tsugita et al. |
| 6,045,547 | A | 4/2000 | Ren et al. |
| 6,051,014 | A | 4/2000 | Jang |
| 6,080,140 | A | 6/2000 | Swaminathan et al. |
| 6,083,239 | A | 7/2000 | Addis |
| 6,096,053 | A | 8/2000 | Bates |
| 6,099,534 | A | 8/2000 | Bates et al. |
| 6,120,494 | A | 9/2000 | Jonkman |
| 6,126,673 | A | 10/2000 | Kim et al. |
| 6,129,739 | A | 10/2000 | Khosravi |
| 6,142,987 | A | 11/2000 | Tsugita |
| 6,146,396 | A | 11/2000 | Konya |
| 6,152,946 | A | 11/2000 | Broome et al. |
| 6,171,328 | B1 | 1/2001 | Addis |
| 6,179,851 | B1 | 1/2001 | Barbut et al. |
| 6,179,861 | B1 | 1/2001 | Khosravi et al. |
| 6,203,561 | B1 | 3/2001 | Ramee et al. |
| 6,214,026 | B1 | 4/2001 | Lepak et al. |
| 6,235,045 | B1 | 5/2001 | Barbut et al. |
| 6,245,087 | B1 | 6/2001 | Addis |
| 6,245,088 | B1 | 6/2001 | Lowery |
| 6,245,089 | B1 | 6/2001 | Daniel et al. |
| 6,264,663 | B1 | 7/2001 | Cano |
| 6,270,513 | B1 | 8/2001 | Tsugita et al. |
| 6,277,138 | B1 | 8/2001 | Levinson et al. |
| 6,287,321 | B1 | 9/2001 | Jang |
| 6,290,710 | B1 | 9/2001 | Cryer et al. |
| 6,309,399 | B1 | 10/2001 | Barbut et al. |
| 6,325,815 | B1 | 12/2001 | Kusleika et al. |
| 6,336,934 | B1 | 1/2002 | Gilson et al. |
| 6,336,116 | B1 | 2/2002 | Brooks et al. |
| 6,361,545 | B1 | 3/2002 | Macoviak et al. |
| 6,364,900 | B1 | 4/2002 | Heuser |
| 6,371,970 | B1 | 4/2002 | Khosravi |
| 6,371,971 | B1 | 4/2002 | Tsugita et al. |
| 6,375,628 | B1 | 4/2002 | Zadno-Azizi et al. |
| 6,383,174 | B1 | 5/2002 | Eder |
| 6,383,205 | B1 | 5/2002 | Samson |
| 6,440,120 | B1 | 8/2002 | Maahs |
| 6,454,799 | B1 | 9/2002 | Schreck |
| 6,485,502 | B2 | 11/2002 | Don Michael |
| 6,499,487 | B1 | 12/2002 | McKenzie et al. |
| 6,517,559 | B1 | 2/2003 | O'Connell |
| 6,530,939 | B1 | 3/2003 | Hopkins et al. |
| 6,537,297 | B2 | 3/2003 | Tsugita et al. |
| 6,544,279 | B1 | 4/2003 | Hopkins et al. |
| 6,558,356 | B2 | 5/2003 | Barbut |
| 6,589,263 | B1 | 7/2003 | Hopkins et al. |
| 6,595,983 | B2 | 7/2003 | Voda |
| 6,605,102 | B1 | 8/2003 | Mazzocchi |
| 6,616,679 | B1 | 9/2003 | Khosravi et al. |
| 6,620,148 | B1 | 9/2003 | Tsugita |
| 6,620,182 | B1 | 9/2003 | Khosravi et al. |
| 6,648,837 | B2 | 11/2003 | Kato et al. |
| 6,663,652 | B2 | 12/2003 | Daniel et al. |
| 6,676,682 | B1 | 1/2004 | Tsugita et al. |
| 6,712,834 | B2 | 3/2004 | Yassour et al. |
| 6,712,835 | B2 | 3/2004 | Mazzocchi |
| 6,719,717 | B1 | 4/2004 | Johnson et al. |
| 6,726,621 | B2 | 4/2004 | Suon et al. |
| 6,726,651 | B1 | 4/2004 | Robinson et al. |
| 6,726,701 | B2 | 4/2004 | Gilson |
| 6,740,061 | B1 | 5/2004 | Oslund |
| 6,817,999 | B2 | 11/2004 | Berube et al. |
| 6,830,579 | B2 | 12/2004 | Barbut |
| 6,843,798 | B2 | 1/2005 | Kusleika et al. |
| 6,872,216 | B2 | 3/2005 | Daniel |
| 6,881,194 | B2 | 4/2005 | Miyata et al. |
| 6,887,258 | B2 | 5/2005 | Denison et al. |
| 6,905,490 | B2 | 6/2005 | Parodi |
| 6,907,298 | B2 | 6/2005 | Smits et al. |
| 6,958,074 | B2 | 10/2005 | Russell |
| 6,969,396 | B2 | 11/2005 | Krolik et al. |
| 7,011,094 | B2 | 3/2006 | Rapacki et al. |
| 7,048,752 | B2 | 5/2006 | Mazzocchi |
| 7,094,249 | B1 | 8/2006 | Broome |
| 7,115,134 | B2 | 10/2006 | Chambers |
| 7,160,255 | B2 | 1/2007 | Saadat |
| 7,169,161 | B2 | 1/2007 | Bonnette et al. |
| 7,169,165 | B2 | 1/2007 | Belef et al. |
| 7,182,757 | B2 | 2/2007 | Miyata et al. |
| 7,214,237 | B2 | 5/2007 | Don Michael |
| 7,278,974 | B2 | 10/2007 | Kato et al. |
| 7,303,575 | B2 | 12/2007 | Ogle |
| 7,306,618 | B2 | 12/2007 | Demond et al. |
| 7,313,445 | B2 | 12/2007 | McVenes et al. |
| 7,323,001 | B2 | 1/2008 | Clubb et al. |
| 7,329,278 | B2 | 2/2008 | Seguin et al. |
| 7,399,308 | B2 | 7/2008 | Borillo et al. |
| 7,410,491 | B2 | 8/2008 | Hopkins |
| 7,493,154 | B2 | 2/2009 | Bonner et al. |
| 7,559,925 | B2 | 7/2009 | Goldfarb et al. |
| 7,572,272 | B2 | 8/2009 | Denison et al. |
| 7,621,904 | B2 | 11/2009 | McFerran et al. |
| 7,722,634 | B2 | 5/2010 | Panetta et al. |
| 7,766,961 | B2 | 8/2010 | Patel et al. |
| 7,918,859 | B2 | 4/2011 | Katoh et al. |
| 7,922,732 | B2 | 4/2011 | Mazzocchi et al. |
| 7,976,562 | B2 | 7/2011 | Bressler et al. |
| 7,998,104 | B2 | 8/2011 | Chang |
| 8,002,790 | B2 | 8/2011 | Brady et al. |
| 8,021,351 | B2 | 9/2011 | Boldenow et al. |
| 8,052,713 | B2 | 11/2011 | Khosravi et al. |
| 8,092,483 | B2 | 1/2012 | Galdonik et al. |
| 8,206,412 | B2 | 6/2012 | Galdonik et al. |
| 8,372,108 | B2 | 2/2013 | Lashinski |
| 8,382,788 | B2 | 2/2013 | Galdonik |
| 8,460,335 | B2 | 6/2013 | Carpenter |
| 8,518,073 | B2 | 8/2013 | Lashinski |
| 8,753,370 | B2 | 6/2014 | Lashinski |
| 8,876,796 | B2 | 11/2014 | Fifer et al. |
| 8,974,489 | B2 | 3/2015 | Lashinski |
| 9,017,364 | B2 | 4/2015 | Fifer et al. |
| 9,055,997 | B2 | 6/2015 | Fifer et al. |
| 9,259,306 | B2 | 2/2016 | Fifer et al. |
| 9,326,843 | B2 | 5/2016 | Lee et al. |
| 9,345,565 | B2 | 5/2016 | Fifer et al. |
| 9,480,548 | B2 | 11/2016 | Carpenter |
| 9,492,264 | B2 | 11/2016 | Fifer et al. |

(56) References Cited

U.S. PATENT DOCUMENTS

| | | |
|---|---|---|
| 9,566,144 B2 | 2/2017 | Purcell et al. |
| 9,636,205 B2 | 5/2017 | Lee et al. |
| 9,943,395 B2 | 4/2018 | Fifer et al. |
| 9,980,805 B2 | 5/2018 | Fifer |
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Herbert et al. |
| 2002/0165573 A1 | 11/2002 | Barbut |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0215230 A1 | 10/2004 | Frazier |
| 2004/0220611 A1 | 11/2004 | Ogle |
| 2004/0225321 A1 | 11/2004 | Krolik et al. |
| 2004/0230220 A1 | 11/2004 | Osborne |
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0136043 A1 | 6/2006 | Cully et al. |
| 2006/0149350 A1 | 7/2006 | Patel et al. |
| 2006/0161241 A1 | 7/2006 | Barbut et al. |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0005131 A1 | 1/2007 | Taylor |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 6/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Chado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0106182 A1 | 4/2010 | Patel et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0211095 A1 | 8/2010 | Carpenter |
| 2010/0228280 A1 | 9/2010 | Groothius et al. |
| 2010/0312268 A1 | 12/2010 | Belson |
| 2010/0324589 A1 | 12/2010 | Carpenter et al. |
| 2011/0066221 A1 | 3/2011 | White et al. |
| 2011/0282379 A1 | 11/2011 | Lee et al. |
| 2012/0046739 A1 | 2/2012 | von Oepen et al. |
| 2012/0095500 A1 | 4/2012 | Heuser |
| 2012/0203265 A1 | 8/2012 | Heuser |
| 2013/0123835 A1 | 5/2013 | Anderson et al. |
| 2013/0131714 A1 | 5/2013 | Wang et al. |
| 2013/0231694 A1 | 9/2013 | Lashinski |
| 2014/0052170 A1 | 2/2014 | Heuser et al. |
| 2014/0094843 A1 | 4/2014 | Heuser |
| 2014/0100597 A1* | 4/2014 | Wang ............. A61F 2/012 606/200 |
| 2014/0249567 A1 | 9/2014 | Adams et al. |
| 2014/0350523 A1* | 11/2014 | Dehdashtian ....... A61M 1/3666 604/509 |
| 2015/0039016 A1 | 2/2015 | Naor et al. |
| 2015/0073533 A1 | 3/2015 | Kassab et al. |
| 2015/0230910 A1 | 8/2015 | Lashinski et al. |
| 2015/0313701 A1* | 11/2015 | Krahbichler ............ 606/300 |
| 2015/0335416 A1 | 11/2015 | Fifer et al. |
| 2016/0058541 A1 | 3/2016 | Schotzko et al. |
| 2016/0262864 A1 | 9/2016 | Von Mangoldt et al. |
| 2016/0310255 A1 | 10/2016 | Purcell et al. |
| 2017/0042658 A1 | 2/2017 | Lee et al. |
| 2017/0112609 A1 | 4/2017 | Purcell et al. |
| 2017/0181834 A1 | 6/2017 | Fifer et al. |
| 2017/0202657 A1 | 7/2017 | Lee et al. |
| 2018/0177582 A1 | 6/2018 | Lashinski |
| 2018/0235742 A1 | 8/2018 | Fields et al. |

FOREIGN PATENT DOCUMENTS

| | | |
|---|---|---|
| EP | 1253871 B1 | 2/2007 |
| EP | 2303384 A2 | 4/2011 |
| EP | 2391303 A2 | 12/2011 |
| EP | 2480165 A2 | 8/2012 |
| EP | 2658476 A1 | 11/2013 |
| EP | 2732794 A1 | 5/2014 |
| EP | 2387427 B1 | 8/2014 |
| EP | 2859864 A1 | 4/2015 |
| JP | 2003505216 A | 2/2003 |
| JP | 2003526451 A | 9/2003 |
| JP | 2003290231 A | 10/2003 |
| JP | 3535098 B2 | 6/2004 |
| JP | 2006500187 A | 1/2006 |
| JP | 2008511401 A | 4/2008 |

(56) References Cited

FOREIGN PATENT DOCUMENTS

| | | | |
|---|---|---|---|
| JP | 2008511401 A1 | 4/2008 |
| JP | 2008515463 A | 5/2008 |
| JP | 2008515463 A1 | 5/2008 |
| JP | 2011525405 A | 9/2011 |
| WO | 9923976 A1 | 5/1999 |
| WO | 0021604 A1 | 4/2000 |
| WO | 0108743 A1 | 2/2001 |
| WO | 0167989 A2 | 9/2001 |
| WO | 2004026175 A1 | 4/2004 |
| WO | 2005118050 A2 | 12/2005 |
| WO | 2006026371 A1 | 3/2006 |
| WO | 2006076505 A2 | 7/2006 |
| WO | 2008033845 A2 | 3/2008 |
| WO | 2008100790 A2 | 8/2008 |
| WO | 2008113857 A2 | 9/2008 |
| WO | 2009032834 A1 | 3/2009 |
| WO | 2010008451 A2 | 1/2010 |
| WO | 2010081025 A1 | 7/2010 |
| WO | 2010083527 A2 | 7/2010 |
| WO | 2010088520 A2 | 8/2010 |
| WO | 2011034718 A2 | 3/2011 |
| WO | 2011017103 A2 | 10/2011 |
| WO | 2012092377 A1 | 7/2012 |
| WO | 2016011267 A1 | 1/2016 |
| WO | 2018156655 A1 | 8/2018 |

OTHER PUBLICATIONS

Internet Archive Wayback Machine; Fiber Innovative Technology: 4DG Fibers; downloaded from http://web.archive.org/web/20011030070010/http://fitfibers.com/4DG_Fibers.htm (Archived Oct. 30, 2001; printed on Dec. 12, 2016).
Internet Archive Wayback Machine; Fiber Innovative Technology: FIT Products; downloaded from http://web.archive.org/web/20010408003529/http://www.fitfibers.com/product.htm (Archived Apr. 8, 2001; printed on Dec. 12, 2016).
International Search Report and Written Opinion dated Aug. 7, 2019 for International Application No. PCT/US2019/029265.

* cited by examiner

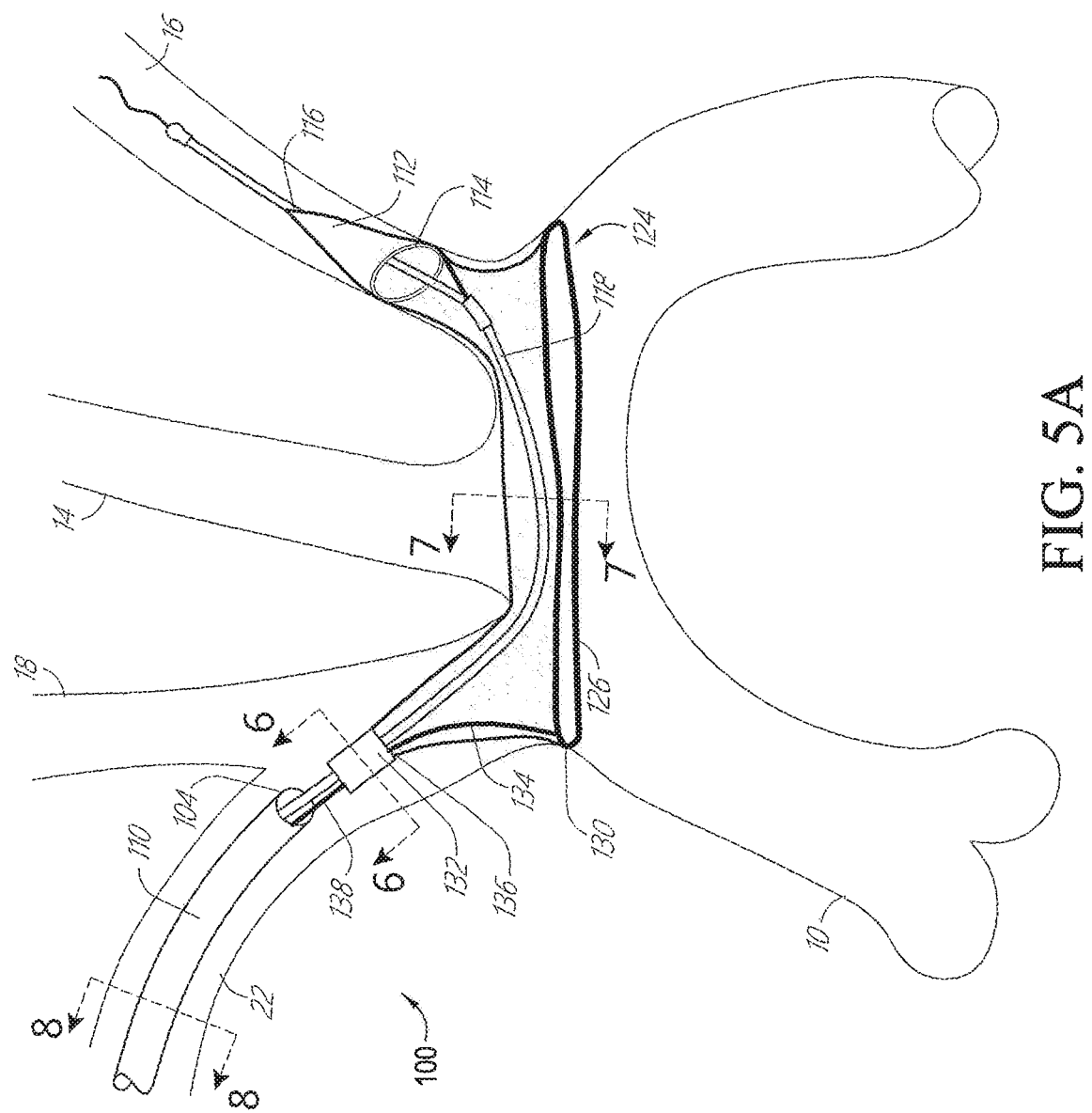

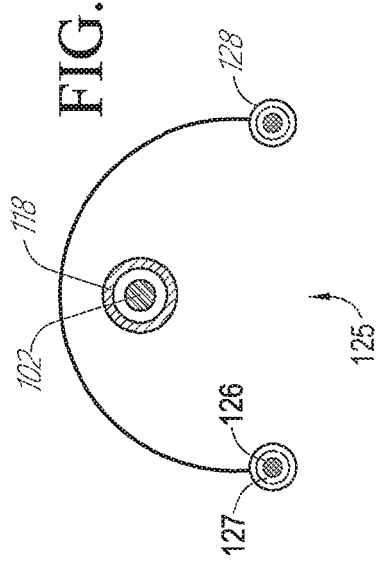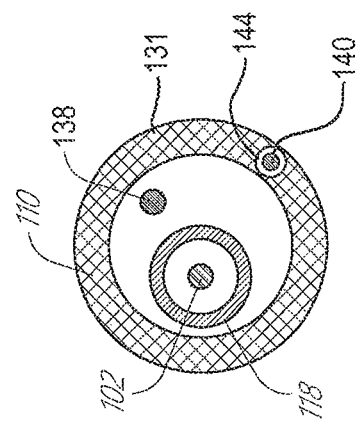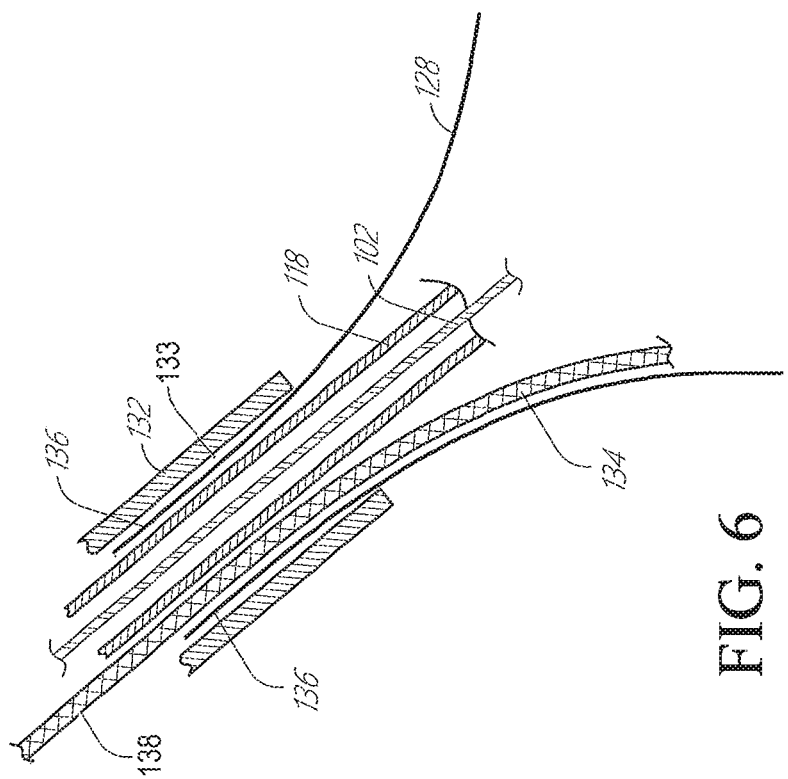

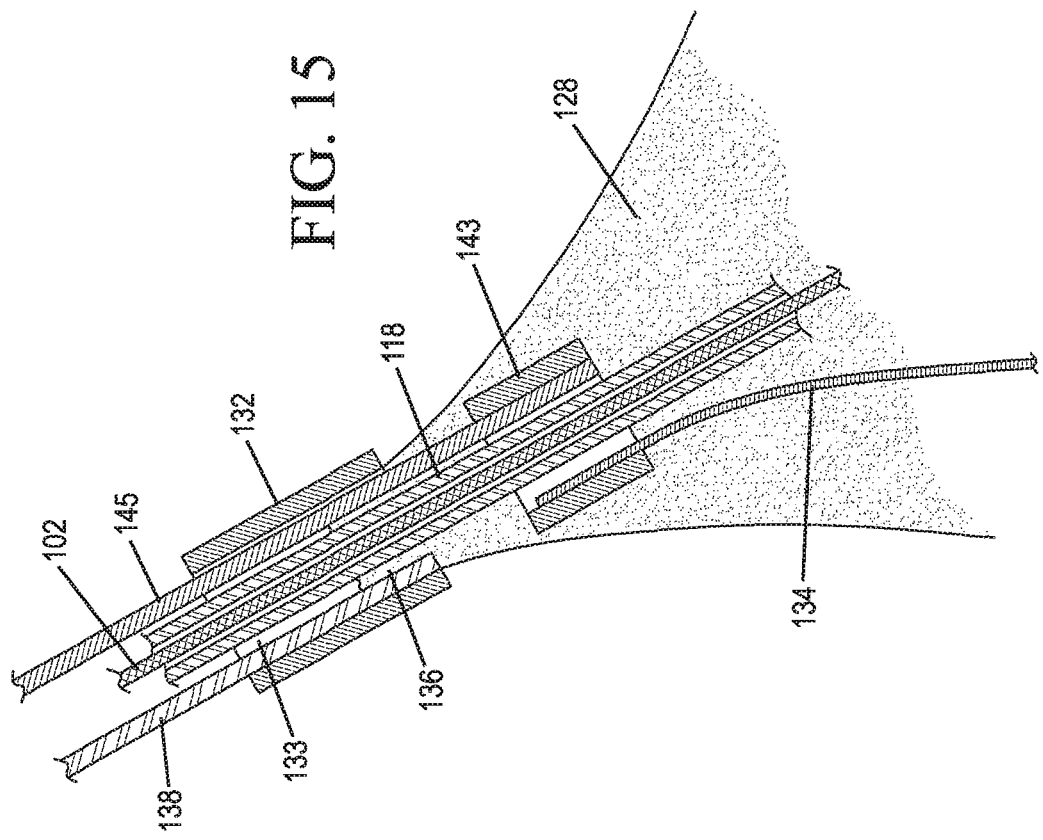
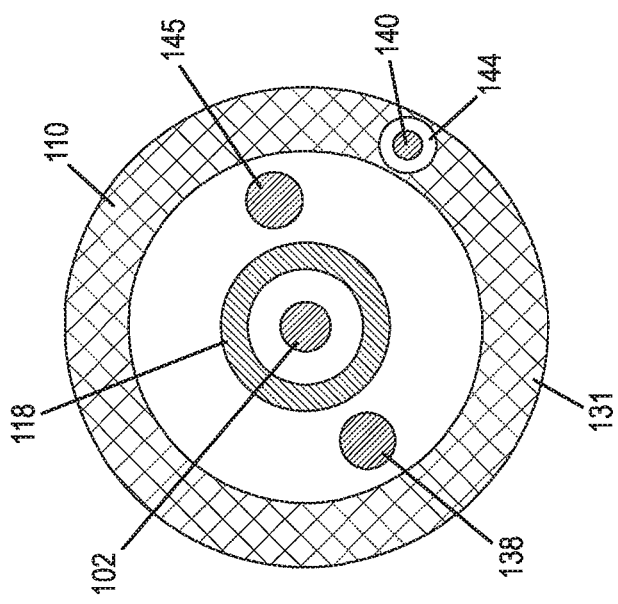

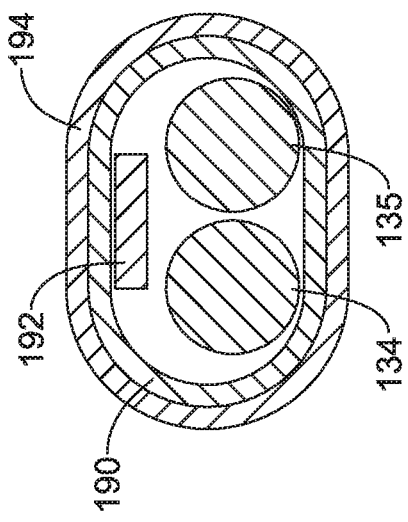
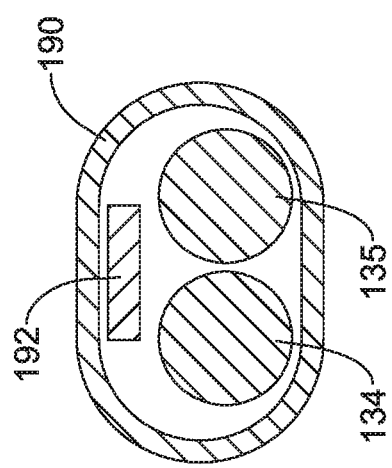
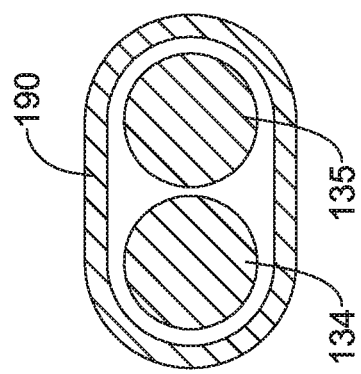

SYSTEMS AND METHODS FOR PROTECTING THE CEREBRAL VASCULATURE

CROSS-REFERENCE TO RELATED APPLICATIONS

This application claims the benefit of priority under 35 U.S.C. § 119 to U.S. Provisional Application Ser. No. 62/663,117, filed Apr. 26, 2018, the entirety of which is incorporated herein by reference.

TECHNICAL FIELD

In general, the present disclosure relates to medical devices for filtering blood. And, more particularly, in certain embodiments, to a method and a system of filters and deflectors for protecting the cerebral arteries from emboli, debris and the like dislodged during an endovascular or cardiac procedure.

BACKGROUND

Thromboembolic disorders, such as stroke, pulmonary embolism, peripheral thrombosis, atherosclerosis, and the like affect many people. These disorders are a major cause of morbidity and mortality in the United States and throughout the world. Thromboembolic events are characterized by an occlusion of a blood vessel. The occlusion can be caused by a clot which is viscoelastic (jelly-like) and comprises platelets, fibrinogen, and other clotting proteins.

Percutaneous aortic valve replacement procedures have become popular, but stroke rates related to this procedure are between four and twenty percent. During catheter delivery and valve implantation, plaque or other material may be dislodged from the vasculature and may travel through the carotid circulation and into the brain. When an artery is occluded by a clot or other embolic material, tissue ischemia (lack of oxygen and nutrients) develops. The ischemia progresses to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Various surgical or endovascular techniques and medicaments to remove or dissolve obstructing material have been developed, to reestablish blood flow. However, additional procedures may be traumatic and are best avoided when possible. Additionally, the use of certain devices carry risks such as the risk of dislodging foreign bodies, damaging the interior lining of the vessel as the catheter is being manipulated, blood thinning, etc.

A variety of filtration or deflection devices have been proposed, to prevent entry of debris into the cerebral circulation. Some isolate only the brachiocephalic artery and left common carotid, while others might additionally isolate the left Subclavian but typically through the use of multiple catheters. Others are said to isolate all three arteries leading to the cerebral circulation, from a single catheter, but the catheter is introduced via the femoral artery and none have achieved adoption.

The need thus remains for a simple, single catheter to enable endovascular isolation of the complete cerebral circulation, preferably from an access point other than the femoral artery.

SUMMARY

The present invention provides a three vessel cerebral protection catheter, for introduction through the brachiocephalic artery via the right radial or right brachial artery, and across the aortic arch. A distal element of the catheter is anchored in the left subclavian artery, and a membrane is deployed such that the single catheter isolates all three of the left subclavian, left common carotid and brachiocephalic arteries from embolic debris that might flow through the aortic arch.

In one implementation, a catheter may comprise an elongate flexible tubular sheath, having a proximal end and a distal end, and an inner member extending through the sheath and moveable relative to the sheath, and supporting a left subclavian element. A filter membrane may be carried between the inner member and the sheath, the membrane and the left subclavian element configured to isolate the aorta from the brachiocephalic, left common carotid and left subclavian arteries when the left subclavian element is expanded within the left subclavian artery and the sheath is retracted to expose the membrane. An aortic support hoop may be provided, configured to seal the membrane against the wall of the aorta.

The left subclavian element may comprise a self-expanding frame and may carry a filter membrane which may have a conical configuration. The catheter may further comprise at least one pull wire for laterally deflecting a distal steering zone on the sheath.

There is also provided a method of isolating the cerebral circulation from embolic debris. The method may comprise the steps of advancing a catheter through the brachiocephalic artery and into the left subclavian artery; deploying an anchor within the left subclavian artery; and retracting an outer sheath on the catheter to expose a filter extending from the anchor, across the ostium to the left common carotid artery and into the brachiocephalic artery. The filter may comprise a body, a peripheral edge and a self-expandable frame carried by at least a portion of the peripheral edge; wherein the frame brings the edge into proximity of the wall of the aorta in response to the retracting step. The frame may be in the form of a loop.

The step of advancing a catheter may include the step of proximally retracting a pull wire to laterally deflect a distal portion of the catheter to enter the ostium of the left subclavian artery. The anchor may be carried by a tubular inner member, and the retracting step may comprise retracting the outer sheath relative to the inner member to expose the anchor. The deploying an anchor step may comprise deploying a self-expandable frame, and the self-expandable frame may carry a left subclavian filter.

In a first example, an embolic protection system for isolating the cerebral vasculature may comprise an elongate outer sheath, having a proximal end and a distal end, an inner member extending through a lumen of the outer sheath, a distal anchoring mechanism coupled to a distal end region of the inner member, a proximal filter membrane carried between the inner member and the outer sheath, the proximal filter membrane configured to extend from the left subclavian artery to the brachiocephalic artery, an aortic support hoop coupled to the proximal filter membrane and configured to seal the proximal filter membrane against the wall of the aorta, and a handle including a first actuation mechanism coupled to proximal end of the inner member and a second actuation mechanism coupled to the proximal end of the outer sheath.

Alternatively or additionally to any of the examples above, in another example, the distal anchoring mechanism comprise a self-expanding frame.

Alternatively or additionally to any of the examples above, in another example, the embolic protection system may further comprise a distal filter membrane coupled to the self-expanding frame.

Alternatively or additionally to any of the examples above, in another example, the embolic protection system may further comprise a proximal bond tube coupled to a proximal filter bag termination of the proximal filter membrane.

Alternatively or additionally to any of the examples above, in another example, the embolic protection system may further comprise an aortic ring connector extending from a proximal end of the aortic ring to proximal bond tube.

Alternatively or additionally to any of the examples above, in another example, the embolic protection system may further comprise a delivery wire coupled to the tube and extending proximally to the handle.

Alternatively or additionally to any of the examples above, in another example, the handle may further comprise a third actuation mechanism coupled to a proximal end of the delivery wire.

Alternatively or additionally to any of the examples above, in another example, the inner member may be slidably disposed within a lumen of the proximal bond tube.

Alternatively or additionally to any of the examples above, in another example, the embolic protection system may further comprise a distal support strut extending between a distal end of the aortic ring and the self-expanding frame of the distal anchoring mechanism.

Alternatively or additionally to any of the examples above, in another example, the embolic protection system may further comprise an aortic ring connector extending from a proximal end of the aortic ring to a connection tube disposed about the inner member and the aortic ring connector, the connection tube distal to a proximal filter bag termination of the proximal filter membrane.

Alternatively or additionally to any of the examples above, in another example, the embolic protection system may further comprise a proximal bond tube coupled to the proximal bag termination of the proximal filter membrane and a delivery wire coupled to the proximal bond tube and extending proximally to the handle.

Alternatively or additionally to any of the examples above, in another example, the embolic protection system may further comprise an aortic ring deployment wire coupled to the aortic ring connector and extending proximally to the handle.

Alternatively or additionally to any of the examples above, in another example, the outer sheath, the inner member, the delivery wire, and the aortic ring deployment wire may be individually actuatable.

Alternatively or additionally to any of the examples above, in another example, a distal end region of the outer sheath may be deflectable.

Alternatively or additionally to any of the examples above, in another example, a cross-sectional shape of the inner member adjacent to the proximal bond tube may be non-circular and at least a portion of the proximal bond tube may have a non-circular cross-sectional shape.

In another illustrative example, an embolic protection system for isolating the cerebral vasculature may comprise an elongate outer sheath, having a proximal end and a distal end, an inner member extending through a lumen of the outer sheath, a distal filter assembly coupled to a distal end region of the inner member, the distal filter assembly including a self-expanding frame and a distal filter membrane coupled to the self-expanding frame, a proximal filter membrane carried between the inner member and the outer sheath, the proximal filter membrane configured to extend from the left subclavian artery to the brachiocephalic artery, an aortic support hoop coupled to the proximal filter membrane and configured to seal the proximal filter membrane against the wall of the aorta, a proximal bond tube coupled to a proximal filter bag termination of the proximal filter membrane, an aortic ring connector coupled to and extending between a proximal end of the aortic ring and the proximal bond tube, a delivery wire coupled to and extending proximally from the proximal bond tube, and a handle including a first actuation mechanism coupled to proximal end of the inner member, a second actuation mechanism coupled to the proximal end of the outer sheath, and a third actuation mechanism coupled to a proximal end of the delivery wire.

Alternatively or additionally to any of the examples above, in another example, the embolic protection system may further comprise a distal anchoring structure positioned distal to the distal filter assembly.

Alternatively or additionally to any of the examples above, in another example, the aortic ring connector may include a curved shape.

In another example, a method of isolating cerebral circulation from embolic debris may comprise advancing an embolic protection system through the brachiocephalic artery and into the left subclavian artery, deploying a distal anchor within the left subclavian artery, and retracting an outer sheath of the embolic protection system to expose a filter extending from the distal anchor, across the ostium to the left common carotid artery and into the brachiocephalic artery.

Alternatively or additionally to any of the examples above, in another example, the distal anchor may be carried by an inner member, the inner member separately actuatable from the outer sheath.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which:

FIG. 5A illustrates a first embodiment of a filter system.

FIG. 6 is a partial cross-sectional view of the illustrative filter system of FIG. 5A, taken at line 6-6.

FIG. 7 is a cross-sectional view of the illustrative filter system of FIG. 5A, taken at line 7-7.

FIG. 8 is a cross-sectional view of the illustrative filter system of FIG. 5A, taken at line 8-8.

FIG. 14 is a cross-sectional view of the illustrative filter system of FIG. 13, taken at line 13-13.

FIG. 15 is a partial cross-sectional view of the illustrative filter system of FIG. 13, taken at line 15-15.

FIGS. 22A-22C illustrate alternative aortic ring connector configurations.

Figure 1:
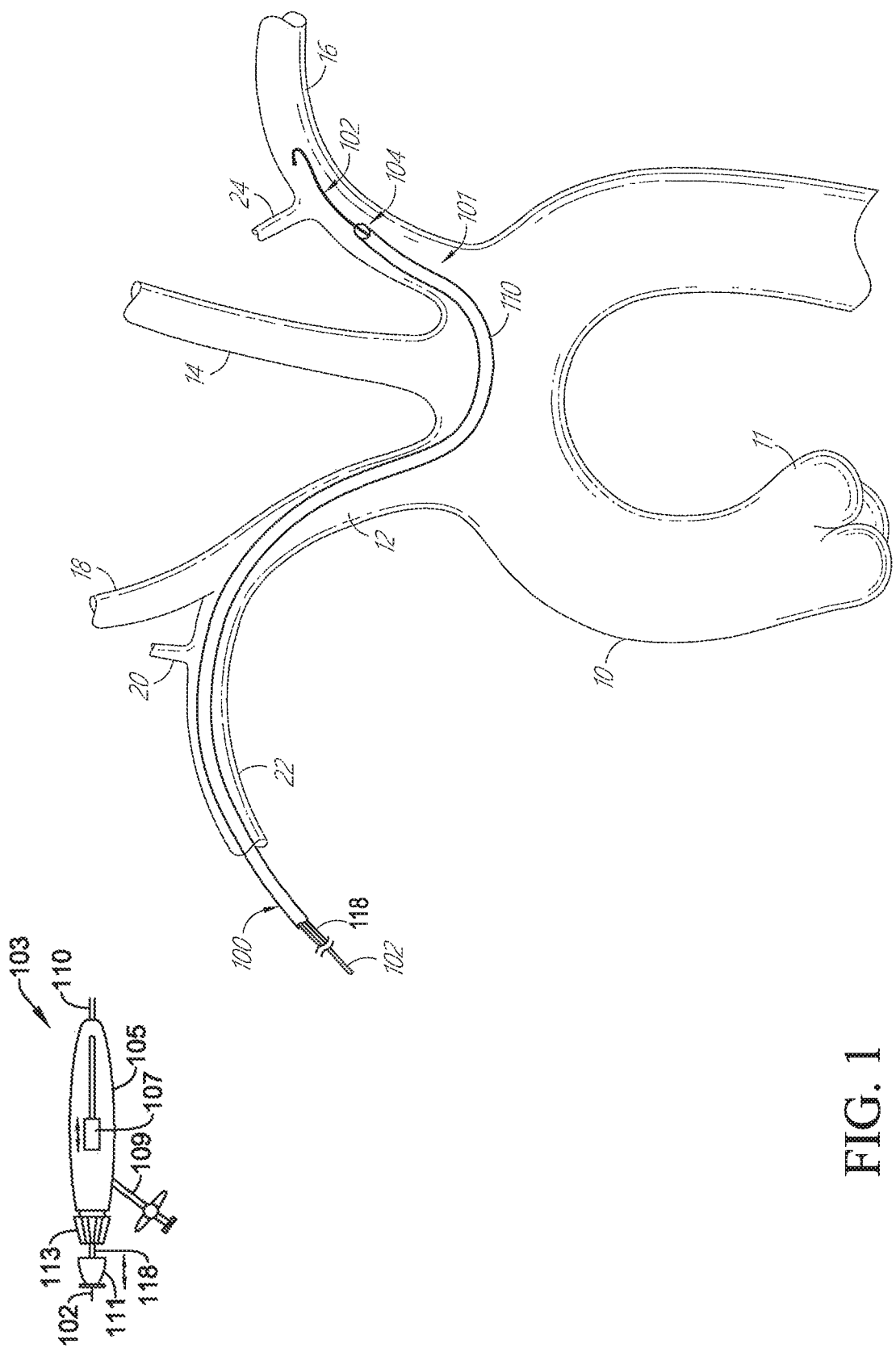
FIGS. 1-4 illustrate a method deploying a filter system to protect the cerebral vascular architecture.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimension ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The disclosure generally relates to devices and methods for filtering fluids and/or deflecting debris contained within fluids, including body fluids such as blood. The filtering or deflecting device can be positioned in an artery upstream from the brain before and/or during an endovascular procedure (e.g., transcatheter aortic valve implantation (TAVI) or replacement (TAVR), transcatheter mitral valve implantation (TAMI) or replacement (TAMR), surgical aortic valve replacement (SAVR), other surgical valve repair, implantation, or replacement, cardiac ablation (e.g., ablation of the pulmonary vein to treat atrial fibrillation) using a variety of energy modalities (e.g., radio frequency (RF), energy, cryo, microwave, ultrasound), cardiac bypass surgery (e.g., open-heart, percutaneous), transthoracic graft placement around the aortic arch, valvuloplasty, etc.) to inhibit or prevent embolic material such as debris, emboli, thrombi, etc. resulting from entering the cerebral vasculature.

Devices and methods have been developed to filter blood flowing to the innominate artery and the left common carotid artery, which provide about 90% of the blood entering the cerebral vasculature. Examples are provided in U.S. Pat. No. 8,876,796, which is herein incorporated by reference in its entirety. Certain such devices and methods leave the left subclavian artery, and thus the left vertebral artery, which provides about 10% of the blood entering the cerebral vasculature, exposed to potential embolic material. Other embodiments described in U.S. Pat. No. 8,876,796 filter blood flowing to the left common carotid artery and the left subclavian artery 16. Certain such devices and methods leave the innominate artery 12, and thus both the right common carotid artery 18 and the right vertebral artery 20, which provide even about 50% of the blood entering the cerebral vasculature, exposed to potential embolic material. Assuming perfect use and operation, either of these options may leave potential stroke rates as high as two to ten percent due to exposed arteries that provide blood flow to the cerebral vasculature.

Several single-access multi-vessel embodiments of cerebral protection devices that can provide full cerebral protection (e.g., protecting all four blood vessels supplying blood to the brain) with minimal arch interference are described below. The devices may be used to trap and/or deflect particles in other blood vessels within a subject, and they can also be used outside of the vasculature. The devices described herein are generally adapted to be delivered percutaneously to a target location within a subject but can be delivered in any suitable way and need not be limited to minimally-invasive procedures.

FIG. 1 is a schematic view of an aortic arch 10. The aortic arch 10 is downstream of the aortic valve 11. The aortic arch 10 typically includes three great branch arteries: the brachiocephalic artery or innominate artery 12, the left common carotid artery 14, and the left subclavian artery 16. The innominate artery 12 branches to the right carotid artery 18, then the right vertebral artery 20, and thereafter is the right subclavian artery 22. The right subclavian artery 22 supplies blood to and may be directly accessed from (termed right radial access) the right arm. The left subclavian artery 16 branches to the left vertebral artery 24, usually in the shoulder area. The left subclavian artery 16 supplies blood to and may be directly accessed from (termed left radial access) the left arm.

Four of the arteries illustrated in FIG. 1 supply blood to the cerebral vasculature: (1) the left carotid artery 14 (about 40% of cerebral blood supply); (2) the right carotid artery 18 (about 40% of cerebral blood supply); (3) the right vertebral artery 20 (about 10% of cerebral blood supply); and (4) the left vertebral artery 24 (about 10% of cerebral blood supply). The devices and methods described herein are also compatible with the prevalent (27%) bovine variant.

FIG. 1 additionally illustrates an example three vessel protection system 100, extending via right radial access across the top of the aortic arch and into the left subclavian artery 16. While the illustrative protection system 100 is described as introduced via right radial access, it is contemplated that the protection system 100 may also be advanced via left radial access. In such an instance, the protection system 100 may be advanced from the left subclavian artery across the top of the aortic arch 10 and into the innominate artery 12.

Figures 2, 2A:
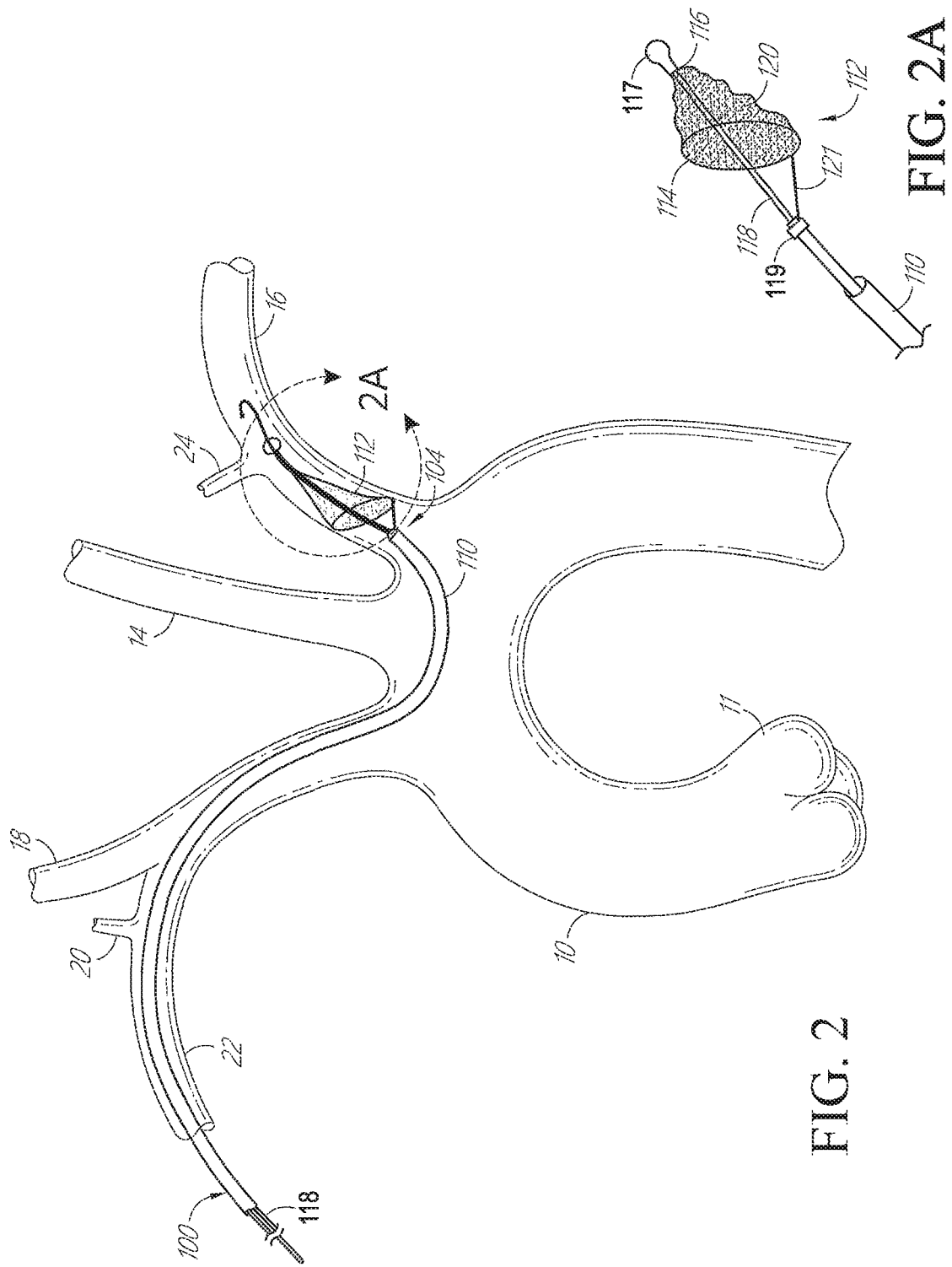
Figure 3:
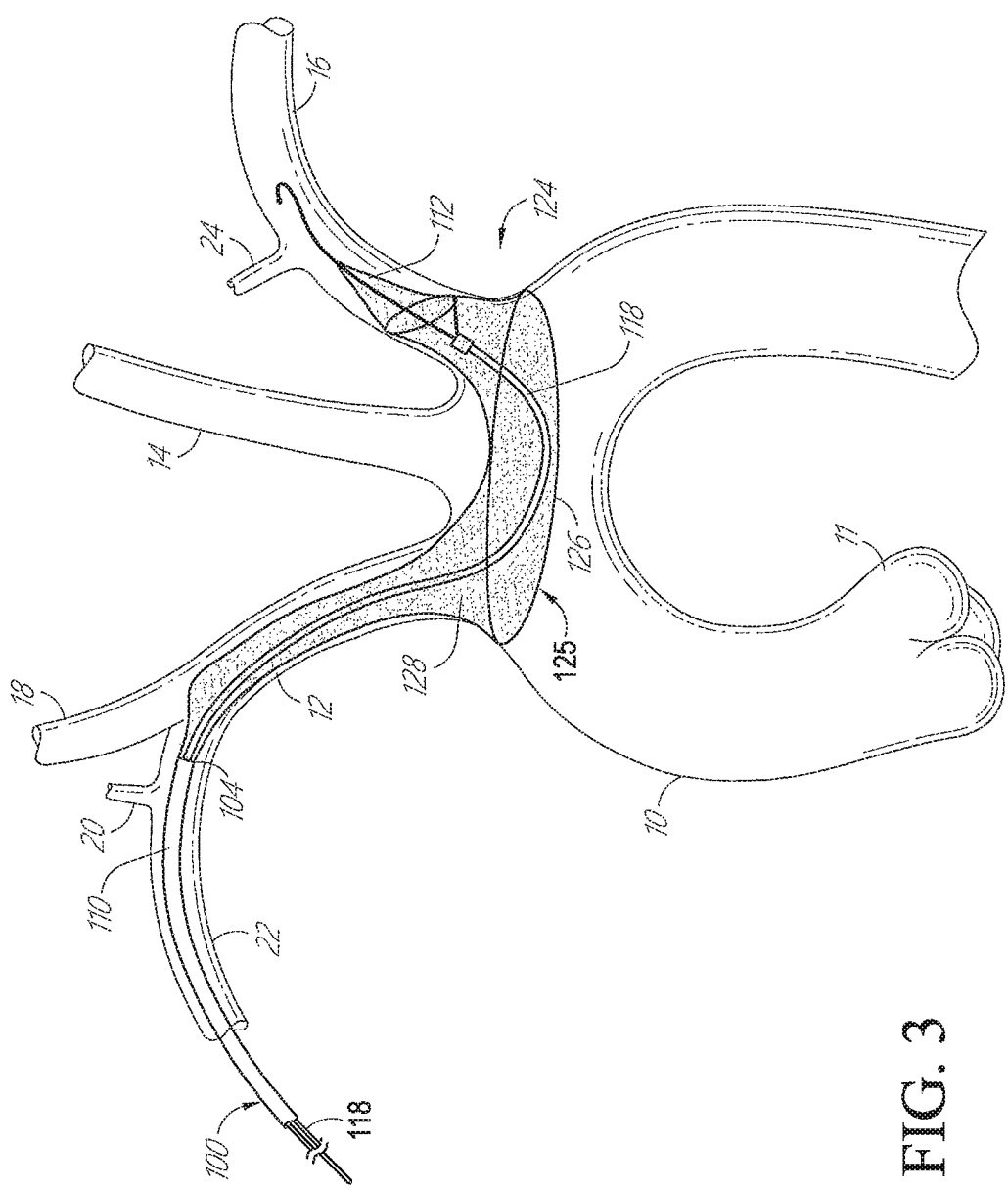

Generally, the protection system 100 may include an outer sheath 110, an inner member 118, a guidewire 102, a distal filter assembly 112 (see, for example, FIG. 2), and a proximal filter assembly 124 (see, for example, FIG. 3). The outer sheath 110 and the inner member 118 may be guided over the guidewire 102, or along the guidewire 102 (in a rapid exchange configuration) to position a distal end of the outer sheath 110 within the left subclavian artery 16. The inner member 118 may be radially inward of the outer sheath 110 and separately actuatable therefrom (e.g., slidably disposed within a lumen of the outer sheath 110). It is contemplated that the guidewire 102 may be positioned within a lumen of the inner member 118 or within a lumen of the outer sheath 110, as desired. In some cases, the lumen of the inner member 118 may be configured to receive a 0.014" (0.3556 millimeter) diameter guidewire 102, although other diameter guidewires 102 may be used, as desired. Each of the guidewire 102, the outer sheath 110, and the inner member 118 may be separately actuatable.

The protection system 100 may include a distal end region 101 and a proximal end region 103. The guidewire 102, the outer sheath 110, and the inner member 118 may be configured to extend from the proximal end region 103 to the distal end region 101. The proximal end region 103 may be configured to be held and manipulated by a user such as a surgeon. The distal end region 101 may be configured to be positioned at a target location such as, but not limited to, the left subclavian artery 16 (or the innominate artery 12 for a left radial access procedure). The proximal end region 103 may include a 105, a control 107 such as a slider, the outer sheath 110, a port 109, an inner member translation control 111, such as a knob, and a hemostasis valve control 113 such as a knob. In some embodiments, the handle 105 may include fewer or more control elements than those illustrated in FIG. 1. For example, the handle 105 may include controls such that the inner member 118 may be translated (e.g., distally advanced or proximally retracted) relative to the outer sheath 110 and/or the handle 105, the outer sheath 110 can be translated relative to the handle 105 and/or the inner member 118, the outer sheath 110 can be bent or deflected, etc. The handle 105 may include other controls for translating and/or deflecting other components of the system 100, as will be described herein. The proximal end region 103 may also include the inner member 118 radially inward of the outer sheath 110. While not explicitly shown, the proximal end region 103 may also include a filter wire (not explicitly shown in FIG. 1) radially inward of the outer sheath 110 (and sometimes radially outward of the inner member 118). Some illustrative filter wires are described in commonly assigned U.S. Pat. No. 9,566,144, the entirety of which is hereby incorporated by reference.

The slider 107 can be used to translate the outer sheath 110 and/or a filter assembly (not explicitly shown in FIG. 1). For example, the slider 107 may proximally retract the outer sheath 110, the slider 107 may distally advance the filter assembly out of the outer sheath 110, or the slider 107 may proximally retract the outer sheath 110 and distally advance the filter assembly (e.g., simultaneously or serially), which can allow the filter assembly to radially expand, which will be described in more detail herein. The slider 107 may also be configured to have an opposite translation effect, which can allow the filter assembly to be radially collapsed (e.g., due to compression by the outer sheath 110) as the filter assembly is drawn into the outer sheath 110. Other deployment systems are also possible, for example comprising gears or other features such as helical tracks (e.g., configured to compensate for any differential lengthening due to foreshortening of the filter assembly, configured to convert rotational motion into longitudinal motion), a mechanical element, a pneumatic element, a hydraulic element, etc. for opening and/or closing the filter assembly. The slider 107 may be independent of the inner member 118 such that the inner member 118 is longitudinally movable independent of the outer sheath 110 (and/or the filter wire). The inner member translation control 111 can be used to longitudinally translate the inner member 118, for example before, after, and/or during deployment of the filter assembly. An inner member translation control 111 may comprise a slider in the handle 105 (e.g., separate from the slider 107).

A port 109 may be in fluid communication with the outer sheath 110 (e.g., via a Y-shaped connector in the handle 105). The port 109 can be used to flush the device (e.g., with saline) before, during, and/or after use, for example to remove air. The port 109 can additionally, or alternatively, be used to monitor blood pressure at the target location, for example, by connecting an arterial pressure monitoring device in fluid communication with a lumen of the outer sheath 110. The port 109 can be also or alternatively be used to inject contrast agent, dye, thrombolytic agents such as tissue plasminogen activator (t-PA), etc.

A rotatable hemostasis valve control 113 can be used to reduce or minimize fluid loss through the protection system 100 during use. For example, a proximal portion and/or intermediate region of the protection system may be positioned in the right subclavian artery 22 and the direction of blood flow with respect to the system 100 will be distal to proximal, so blood may be otherwise inclined to follow the pressure drop out of the system 100. The hemostasis valve control 113 is illustrated as being rotatable, but other arrangements are also possible (e.g., longitudinally displaceable). The hemostasis valve control 113 may be configured to fix relative positions of the outer sheath 110 and the filter assembly, for example as described with respect to the hemostasis valve in U.S. Pat. No. 8,876,796. The hemostasis valve 113 may comprise, for example, an elastomeric seal and HV nut.

To position the protection system 100 within the body, an incision may be made in the subject's right radial artery, or alternatively the right brachial artery. An introducer (not explicitly shown) may be placed into the incision and the protection system 100 inserted into the introducer. The protection system 100 may be advanced through the vasculature in a delivery configuration in which a filter assembly is collapsed or sheathed within the outer sheath 110. The outer sheath 110, inner member 118, and the filter assemblies 112, 124 may be advanced over a guidewire 102 to the target location. In some cases, the guidewire 102 may be positioned at the target location and the outer sheath 110, inner member 118, and the filter systems 112, 124 subsequently advanced over the guidewire 102 to the target location. In other instances, the guidewire 102 and the outer sheath 110, inner member 118, and the filter systems 112, 124 may be advanced substantially simultaneously with the guidewire 102 leading (e.g., positioned most distal to) the outer sheath 110, inner member 118, and the filter systems 112, 124.

The delivery catheter or outer sheath 110 may have a diameter sized to navigate the vasculature from the incision to the target location. An outer sheath 110 sized for right radial access may have a diameter in the range of about 6 French (F). An outer sheath 110 sized for femoral access may be larger, although this is not required. These are just some examples. In some cases, the outer sheath 110 (or other components of the protection system 100) may include deflectable tip or an articulatable distal tip. It is contemplated that the distal tip of the outer sheath 110 may be deflected (e.g., using the handle 105) to facilitate navigation of the system 100 through the vasculature and cannulation of the target vessel. In some cases, the deflectable tip may be configured to deflect by about 90°. However, the tip of the outer sheath 110 may be made to deflect by less than 90 or more than 90, as desired. As described above, the deflection may be controlled by a rotating knob at the handle 105, or the control mechanism. In some cases, the outer sheath 110 may include a pre-shaped and/or non-deflectable tip.

The left subclavian artery 16 may be cannulated through a combination of advancing and torqueing the catheter 110. In some cases, the left subclavian artery 16 may first be cannulated using the guidewire 102. It is contemplated that in some cases, the deflection of the catheter tip may be relaxed to advance the outer sheath 110 into the left subclavian artery 16. Once the protection system 100 (e.g., the distal end 104 of the outer sheath 110) has been advanced to the target location, which in the illustrated embodiment may be the left subclavian artery 16, the outer sheath 110 may be proximally retracted to expose a distal filter assembly 112 beyond the distal end 104 of the outer sheath 110, as shown in FIG. 2. Alternatively, or additionally, the inner member 118 may be distally advanced to deploy the distal filter assembly 112. The distal filter assembly 112 may be configured to deployed in the distal-most great vessel relative to the location of the incision. For example, when right radial access is used, the distal-most great vessel is the left subclavian artery 16. However, if left radial access is used, the distal-most great vessel is the innominate artery 12.

Referring additionally to FIG. 2A, which illustrates an enlarged view of the distal filter assembly 112, the distal filter assembly 112 may comprise a self-expanding filter assembly (e.g., comprising a superelastic material with stress-induced martensite due to confinement in the outer sheath 110). The distal filter assembly 112 may comprise a shape-memory material configured to self-expand upon a temperature change (e.g., heating to body temperature). The distal filter assembly 112 may comprise a shape-memory or superelastic frame 114 (e.g., comprising a nitinol hoop) and a microporous filter element 120 (e.g., comprising a polymer including laser-drilled holes) coupled to the frame, for example similar to the filter assemblies described in U.S. Pat. No. 8,876,796.

The frame 114 may generally provide expansion support to the filter element 120 in the expanded state. In the expanded state, the filter element 120 is configured to filter fluid (e.g., blood) flowing through the filter element 120 and to inhibit or prevent particles (e.g., embolic material) from flowing through the filter element 120 by capturing the particles in the filter element 120. The frame 114 may configured to anchor the distal filter assembly 112 by engaging or apposing the inner walls of a lumen (e.g., blood vessel) in which the distal filter assembly 112 is expanded. In some cases, the distal filter assembly 112 may also anchor the proximal filter assembly 124. For example. the distal filter assembly 112 may be a distal anchoring mechanism. The anchoring mechanism may include a filter membrane or may lack a filter membrane, as desired. As will be described in more detail herein, other anchoring mechanisms may be provided in addition to or alternatively to the distal filter assembly 112. The frame 114 may comprise or be constructed of, for example, nickel titanium (e.g., nitinol), nickel titanium niobium, chromium cobalt (e.g., MP35N, 35NLT), copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, combinations thereof, and the like. The frame 114 may comprise a wire (e.g., having a round (e.g., circular, elliptical) or polygonal (e.g., square, rectangular) cross-section). For example, in some embodiments, the frame 114 may comprise a straight piece of nitinol wire shape set into a circular or oblong hoop or hoop with one or two straight legs running longitudinally along or at an angle to a longitudinal axis of the distal filter assembly 112. The frame 114 may be coupled to a support strut 121. If so provided, the straight legs may be on a long side of the distal filter assembly 112 and/or on a short side of the distal filter assembly 112. The frame 114 may form a shape of an opening 115 of the distal filter assembly 112. The opening 115 may be circular, elliptical, or any shape that can appropriately appose sidewalls of a vessel such as the left subclavian artery 16. The distal filter assembly 112 may have a generally proximally-facing opening 115. In other embodiments, the opening 115 may be distally facing. For example, the orientation of the opening 115 may vary depending on where the access incision is located.

The frame 114 may include a radiopaque marker such as a small coil wrapped around or coupled to the hoop to aid in visualization under fluoroscopy. In some embodiments, the frame 114 may comprise a shape other than a hoop, for example, a spiral. In some embodiments, the distal filter assembly 112 may not include or be substantially free of a frame.

In some embodiments, the frame 114 and the filter element 120 form an oblique truncated cone having a non-uniform or unequal length around and along the length of the distal filter assembly 112. In such a configuration (e.g., along the lines of a windsock), the filter assembly 112 has a larger opening 115 (upstream) diameter and a reduced ending (downstream) diameter.

The filter element 120 may include pores configured to allow blood to flow through the filter element 120, but that are small enough to inhibit prevent particles such as embolic material from passing through the filter element 120. The filter element 120 may comprise a filter membrane such as a polymer (e.g., polyurethane, polytetrafluoroethylene (PTFE)) film mounted to the frame 114. The filter element 120 may have a thickness between about 0.0001 inches (0.00254 millimeters) and about 0.03 inches (0.76 millimeters) (e.g., no more than about 0.0001 inches (0.00254 millimeters), about 0.001 inches (0.0254 millimeters), about 0.005 inches (0. millimeters), about 0.01 inches (0.254 millimeters), about 0.015 inches (0.381 millimeters), about 0.02 inches (0.51 millimeters), about 0.025 inches (0.635 millimeters), about 0.03 inches (0.76 millimeters), ranges between such values, etc.).

The film may comprise a plurality of pores or holes or apertures extending through the film. The film may be formed by weaving or braiding filaments or membranes and the pores may be spaces between the filaments or membranes. The filaments or membranes may comprise the same material or may include other materials (e.g., polymers, non-polymer materials such as metal, alloys such as nitinol, stainless steel, etc.). The pores of the filter element 120 are configured to allow fluid (e.g., blood) to pass through the filter element 120 and to resist the passage of embolic material that is carried by the fluid. The pores can be circular, elliptical, square, triangular, or other geometric shapes. Certain shapes such as an equilateral triangular, squares, and slots may provide geometric advantage, for example restricting a part larger than an inscribed circle but providing an area for fluid flow nearly twice as large, making the shape more efficient in filtration verses fluid volume. The pores may be laser drilled into or through the filter element 120, although other methods are also possible (e.g., piercing with microneedles, loose braiding or weaving). The pores may have a lateral dimension (e.g., diameter) between about 10 micron (μm) and about 1 mm (e.g., no more than about 10 μm, about 50 μm, about 100 μm, about μm, about 150 μm, about 200 μm, about 250 μm, about 300 μm, about 400 μm, about 500 μm, about 750 μm, about 1 mm, ranges between such values, etc.). Other pore sizes are also possible, for example depending on the desired minimum size of material to be captured.

The material of the filter element 120 may comprise a smooth and/or textured surface that is folded or contracted into the delivery state by tension or compression into a lumen. A reinforcement fabric may be added to or embedded in the filter element 120 to accommodate stresses placed on the filter element 120 during compression. A reinforcement fabric may reduce the stretching that may occur during deployment and/or retraction of the distal filter assembly 112. The embedded fabric may promote a folding of the filter to facilitate capture of embolic debris and enable recapture of an elastomeric membrane. The reinforcement material could comprise, for example, a polymer and/or metal weave to add localized strength. The reinforcement material could be imbedded into the filter element 120 to reduce thickness. For example, imbedded reinforcement material could comprise a polyester weave mounted to a portion of the filter element 120 near the longitudinal elements of the frame 114 where tensile forces act upon the frame 114 and filter element 120 during deployment and retraction of the distal filter assembly 112 from the outer sheath 110.

The distal filter assembly 112 may be coupled (e.g., crimped, welded, soldered, etc.) to a distal end of a deployment wire or filter wire (not explicitly shown) via a strut or wire 121, although this is not required. When both or all of the filter wire and the strut 121 are provided, the filter wire and the strut 121 may be coupled to the inner member 118 proximal to the filter assembly 112 using a crimp mechanism 119. In other embodiments, the filter wire and the strut 121 may be a single unitary structure. The filter wire and/or strut 121 can comprise a rectangular ribbon, a round (e.g., circular, elliptical) filament, a portion of a hypotube, a braided structure (e.g., as described herein), combinations thereof, and the like. A distal filter bag termination 116 or a distal end 116 of the distal filter assembly may also be coupled to the inner member 118. In some cases, the distal end 116 may be coupled to the inner member using a nose cone 117. The nose cone 117 may both secure the distal end 116 of the distal filter assembly 112 and reduce injury and/or vessel perforation during insertion of the system 100. In some cases, the inner member 118 may reduce in diameter in the distal direction. The diameter may be step-wise or gradual.

The distal filter assembly 112 in an expanded, unconstrained state may have a maximum diameter or effective diameter (e.g., if the mouth is in the shape of an ellipse the effective diameter is the diameter of the approximate circular opening 115 of the filter viewed from an end view) The diameter can be between about 1 mm and about 15 mm (e.g., at least about 2 mm, about 4 mm, about 6 mm, about 8 mm, about 10 mm or more, but generally less than about 15 mm or 12 mm or less depending upon the intended target vessel. In some embodiments (e.g., when the distal filter assembly 112 is configured to be positioned in the left subclavian artery 16), the diameter may be between about 7 mm and about 12 mm (e.g., about 7 mm, about 8 mm, about 9 mm, about 10 mm, about 11 mm, about 12 mm, ranges between such values, etc.). In some embodiments (e.g., when the distal filter assembly 112 is configured to be positioned in the left vertebral artery 24), the diameter may be between about 2 mm and about 4.5 mm (e.g., about 2 mm, about 2.5 mm, about 3 mm, about 3.5 mm, about 4 mm, about 4.5 mm, ranges between such values, etc.). Other diameters d or other types of lateral dimensions are also possible. Different diameters can allow treatment of a selection of subjects having different vessel sizes.

The filter assembly 112 may have a maximum length from a proximal limit of hoop 114 to the distal end or point of convergence 116 with the inner member 118. The length can be between about 7 mm and about 50 mm (e.g., at least about 7 mm, about 8 mm, about 10 mm, about 12 mm, 16 mm, about 20 mm or more, but generally less than about 40 mm or 30 mm or 20 mm or less depending upon the intended target vessel. Other lengths are also possible, for example based on the diameter or effective diameter. For example, the length of the distal filter assembly 112 may increase as the diameter increases, and the length of the distal filter assembly 112 may decrease as the diameter decreases.

In the illustrated embodiment, as described herein, the distal filter assembly 112 comprises a self-expanding support such as hoop or frame 114 which supports the open proximal end of an approximately conical filter membrane 120. A support strut 121 may be provided to connect the hoop 114 to a portion of the system 100 such as the inner member 118, to facilitate resheathing of the filter assembly 112 and also to orientate the hoop or frame 114. In the illustrated embodiment, the distal filter assembly 112 may function both to filter blood entering the left subclavian artery 16, and also to anchor the system as will be discussed in more detail herein.

Continued proximal actuation of the outer sheath 110 while fixing the inner member 118 relative to the handle 105 (and thus the deployment wire and proximal bond, as will be described in more detail herein) may then deploy the aortic arch component or proximal filter assembly 124, as shown in FIG. 3. It is contemplated that distal end 104 of the outer sheath 110 may be withdrawn into the innominate artery 12 or the right subclavian artery 22 to fully expose the proximal filter assembly 124. As the outer sheath 110 is withdrawn, the distal filter assembly 112 remains in the left subclavian artery 16, supported by the inner member 118 and helping to anchor the proximal filter assembly 124.

The proximal filter assembly 124 may include an aortic ring 126 or support element and a filter membrane or filter element 128. The aortic ring 126 may be similar in form and function to the frame 114 of the distal filter assembly 112, although larger in scale. Similarly, the filter membrane 128 may be similar in form and function to the filter element 120 described in herein. The aortic ring 126 generally provides expansion support to the filter membrane 128 in its expanded configuration, while the filter membrane 128 is adapted to filter fluid, such as blood, and trap particles flowing therethrough. The aortic ring 126 may include an approximately elliptical hoop of a shape memory wire such as nitinol. The aortic ring 126 may be configured to engage the wall of the aorta and seal against the roof of the aortic arch outside of the ostia of all three great vessels 12, 14, 16 to isolate the cerebral vasculature. For example, the aortic ring 126 may be sized and shaped such that it extends from the ostium of the left subclavian artery 16 to the ostium of the innominate artery 12. The center 125 of the aortic ring 126 is open to allow blood and debris to enter the device 124, and the ring 126 is attached around its perimeter to the filter membrane 128. The aortic ring 126 may be self-expanding such that as the outer sheath 110 is proximally withdrawn, the aortic ring 126 automatically expands, although this is not required. As will be described in more detail herein, the aortic ring 126 may be coupled to different portions of the protection system 100.

Figure 4:
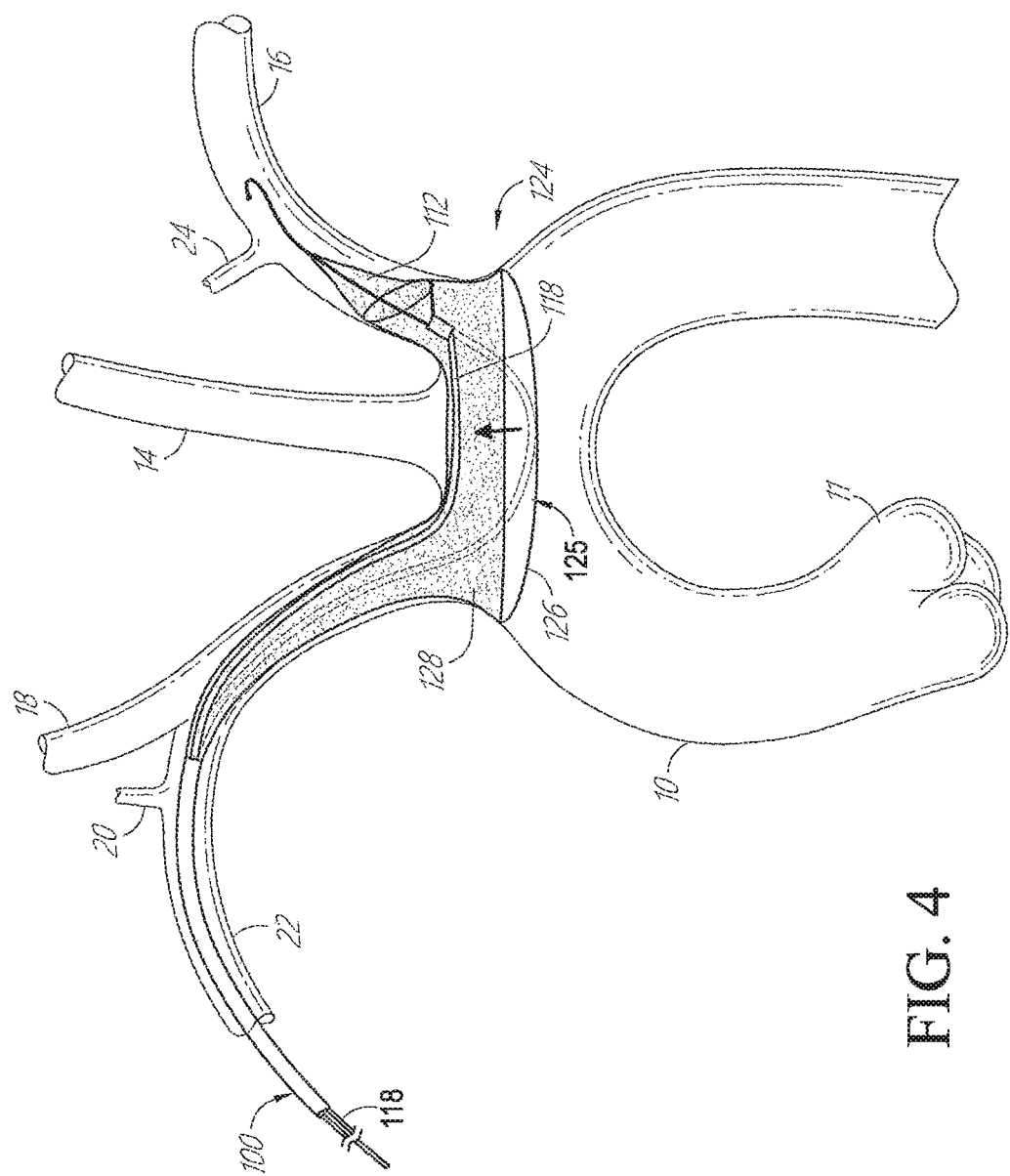

Once the proximal filter assembly 124 has been deployed, the inner member 118 may be retracted to minimize intrusion into the aorta 10, as illustrated in FIG. 4. The position of the inner member 118 may be adjusted using the control 111 at the handle 105. As will be described in more detail herein, the mechanism coupling the proximal filter 124 to the system 100 may be adjusted by proximally retracting or distally advancing the handle 105 to ensure the proximal filter 124 is fully deployed, the aortic ring 126 is apposed to the roof of the aortic arch 10, and the inner member 118 is pulled up against the roof of the aortic arch 10 to ensure that the membrane 128 is fully against the roof of the arch 10. The proximal filter assembly 124 is thus positioned to protect the cerebral vasculature 14, 18, 20, 24 from embolic debris during an endovascular procedure such as TAVR.

Once the protection system 100 has been deployed, the TAVR, or other index procedure, may be performed. Once the index procedure is contemplate, the inner member 118 may be advanced relative to the handle 105 to apply tension to the proximal filter element 128 and/or the distal filter element 120. The outer sheath 110 may then be advanced relative to the handle 105, while fixing the position of the inner member 118 relative to the handle 105, until the proximal filter assembly 124 and the distal filter assembly 112 are fully sheathed. The protection system 100 may then be removed from the introducer sheath.

Figure 5B:
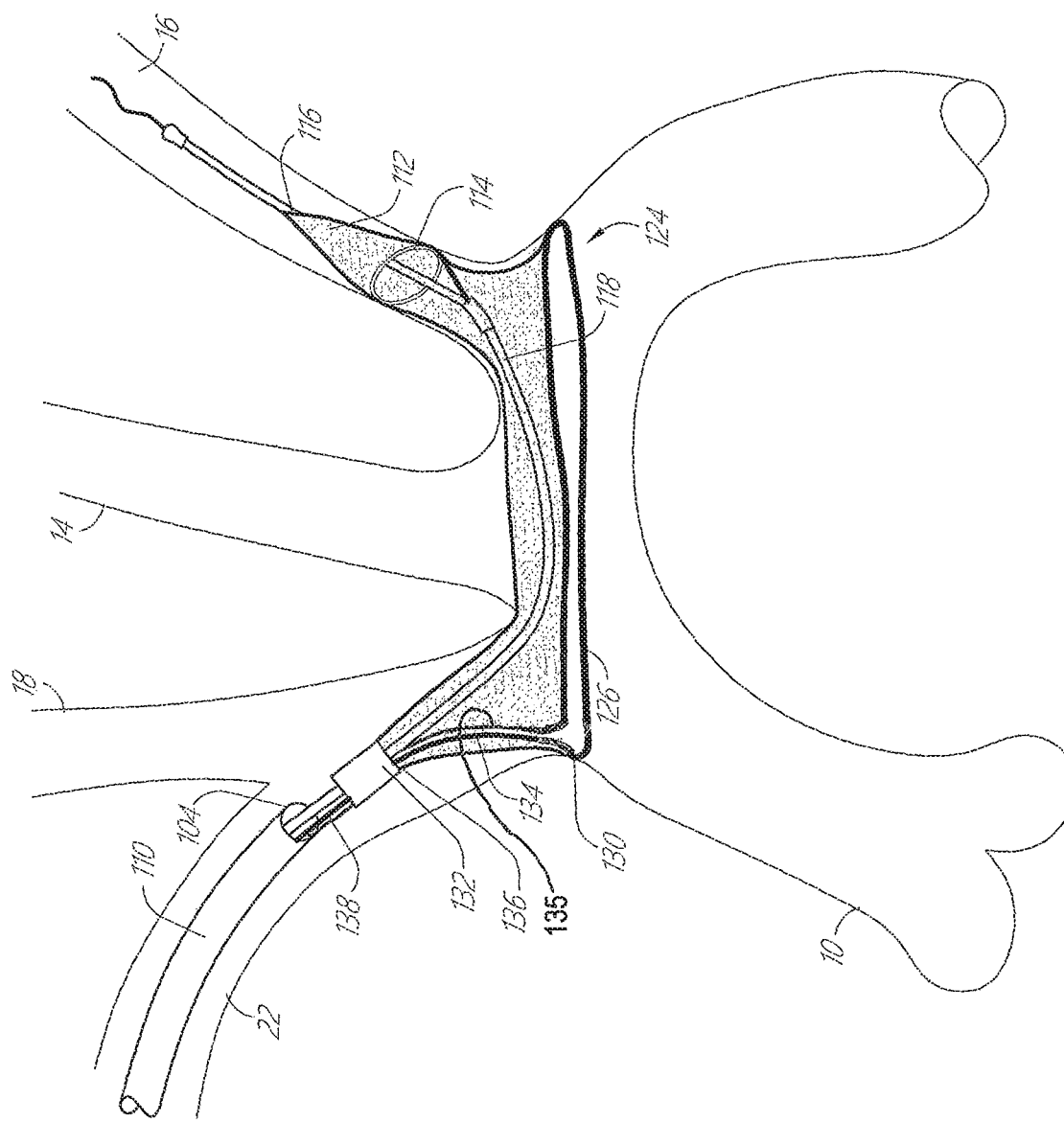
FIG. 5B illustrates another alternative embodiment a filter system.

FIGS. 5A and 5B illustrate a first mechanism for coupling the proximal filter assembly 124 to the protection system. In the illustrated embodiment, a proximal end 130 of the aortic ring 126 is connected to a proximal bond tube 132 with an aortic ring connector 134. The proximal bond tube 132 may be a tubular structure configured to link or couple several structures of the system 100. In some cases, the structures coupled to the proximal bond tube 132 may extend into and be coupled within a lumen of the proximal bond tube 132, as will be described in more detail herein. The aortic ring connector 134 may be formed as a monolithic or unitary structure with the aortic ring 126. Alternatively, the aortic ring connector 134 may be separately formed and coupled with the aortic ring 126. It is contemplated that the aortic ring connector 134 may be formed from a nitinol wire, or other suitable material. The proximal end region 136 of the membrane 128, or the proximal filter bag termination 136, may also be connected to the proximal bond tube 132.

The proximal bond tube 132 may be connected to a delivery wire 138 configured to extend proximally to the handle 105. The handle 105 may include at least three controls (which may be sliding controls) including a control for translation of the inner member 118 relative to the handle 105, a control for translation of the delivery catheter 110 relative to the handle 105 to allow for deployment and retrieval of the filter assemblies 112, 124, and a control for deflection of the distal tip of the delivery catheter 110. The delivery wire 138 is connected to both the proximal bond tube 132 and the handle 105. Thus the aortic ring 126 and proximal filter bag termination 136 positions are fixed relative to the handle 105. As such, the position of the proximal bond tube 132 relative to the patient's body can be moved by either advancing or retracting the handle 105. As described above, the distal filter frame 114, and thus the distal end region 116 of the distal filter element 120 or the distal filter bag termination 116, are connected to the inner member 118, and are advanced and retracted relative to the outer sheath 110 with a first handle control 111. The steerable outer sheath or delivery catheter 110 may be withdrawn relative to the handle 105 to deploy the device using a second handle control 107. The tip 104 of the outer sheath or delivery catheter 110 may be deflected to assist with cannulation of the left subclavian artery 16 (or the brachiocephalic artery 12) using a third handle control (not explicitly shown).

In FIG. 5A, the aortic ring connector 134 may be formed by bonding two proximally extending sections of the wire forming the hoop of aortic ring 126 to produce a single, relatively more rigid strut 134. Alternatively, as shown in FIG. 5B, the two wires 134, 135 which extend proximally from aortic ring 126 may be movable with respect to each other. This allows the minor axis of the aortic ring 126 to self adjust to the aorta 10, as the two wires 134, 135 move towards or away from each other. Either an excess of membrane 128, or overlapping sections of membrane 128 carried by the wires 134, 135 allow continuity of the membrane 128 coverage regardless of the spacing between wires 134 and 135.

FIG. 6 is a partial cross-sectional view of the illustrative system 100 taken at line 6-6 of FIG. 5A. As can be seen, the proximal bond tube 132 defines a lumen 133. The inner member 118 may be sliably disposed within the lumen 133 such that the inner member 118 is separately movable from the proximal bond tube 132. The proximal filter bag termination 136 may be coupled to an inner surface of the proximal bond tube 132. However, other coupling configurations can be used, as desired. Further, the deployment or control wire 138 may also be coupled to the proximal bond. The control wire 138 may be coupled directly to the proximal bond or indirectly coupled (e.g., with the proximal filter bag termination 136 disposed therebetween), as desired. In some cases, the control wire 138 and the aortic ring connector 134 may form a unitary structure. In other embodiments, the deployment or control wire 138 and the aortic ring connector 134 may be separate and distinct components.

FIG. 7 is a cross-sectional view of the protection system 100 taken at line 7-7 of FIG. 5A. As can be seen, the membrane 128 may be coupled to the aortic ring 126 about its perimeter to define an opening for 125 that allows blood and debris to enter the proximal filter assembly 124. The membrane 128 also forms a net that prevents debris from exiting the proximal filter assembly 124. In some cases, the aortic ring 126 may be include a radiopaque coil or marker to facilitate to allow the aortic ring 126 to be visualized.

As described herein, a distal steering segment of steerable delivery catheter 110 may be deflected laterally in response to manipulation of a steering control on the proximal manifold or handle 105. Referring additionally to FIG. 8, which illustrates a cross-sectional view of the illustrative system 100, taken at line 8-8 of FIG. 5A, in the illustrated embodiment, the sidewall of delivery catheter or outer sheath 110 is provided with a pull wire lumen 144 for axially moveably receiving a pull wire 140 which may be proximally retracted to deflect the distal tip laterally. A second pull wire may alternatively be provided, such as at 180 degrees around the catheter 110 from the first pull wire, to facilitate straightening or deflecting the catheter in a second, opposite direction. Further, in some embodiments, the outer sheath 110 may include a reinforcement braid 131, although this is not required.

Figure 9:
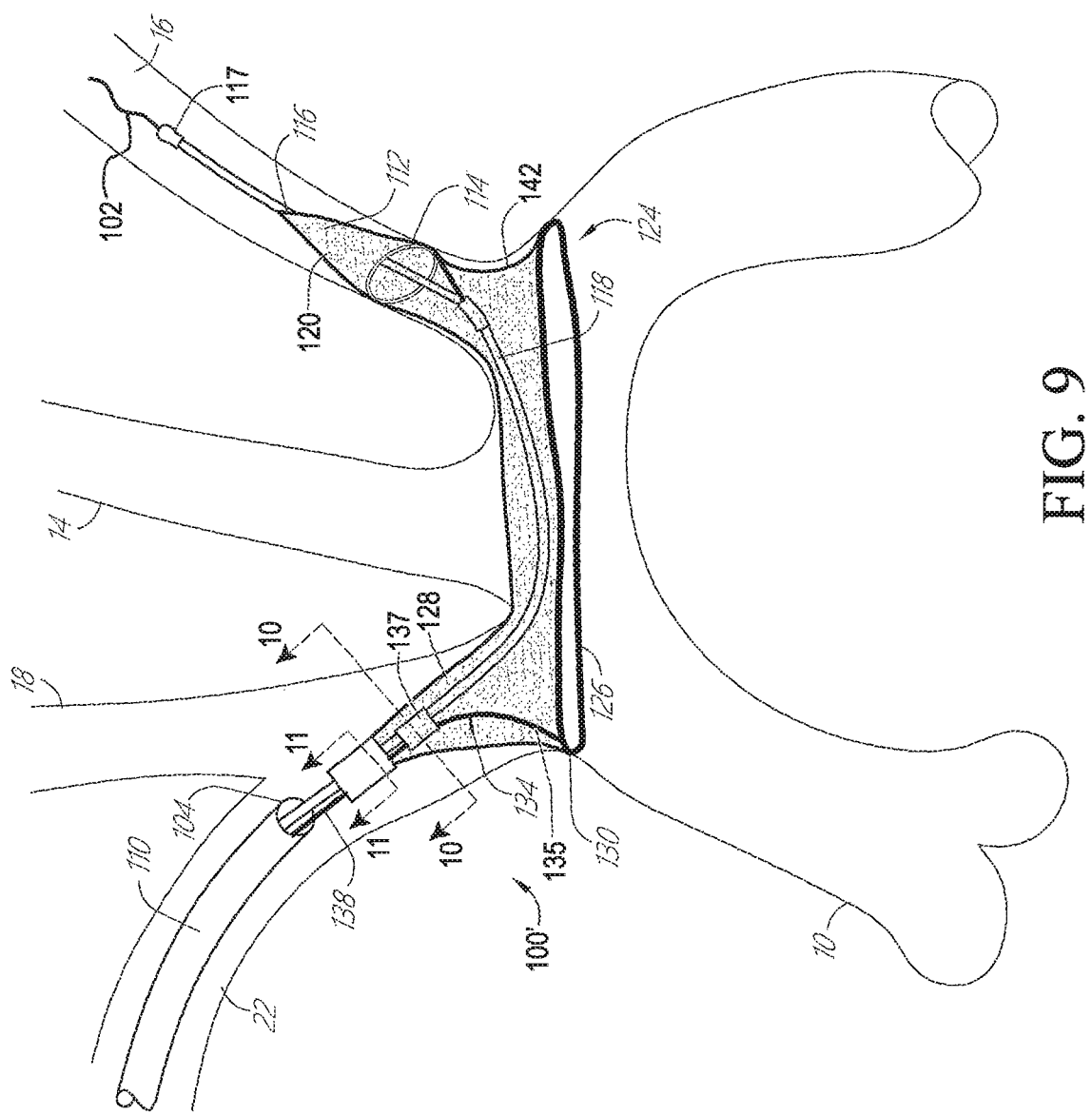
FIG. 9 illustrates another alternative embodiment a filter system.
Figure 11:
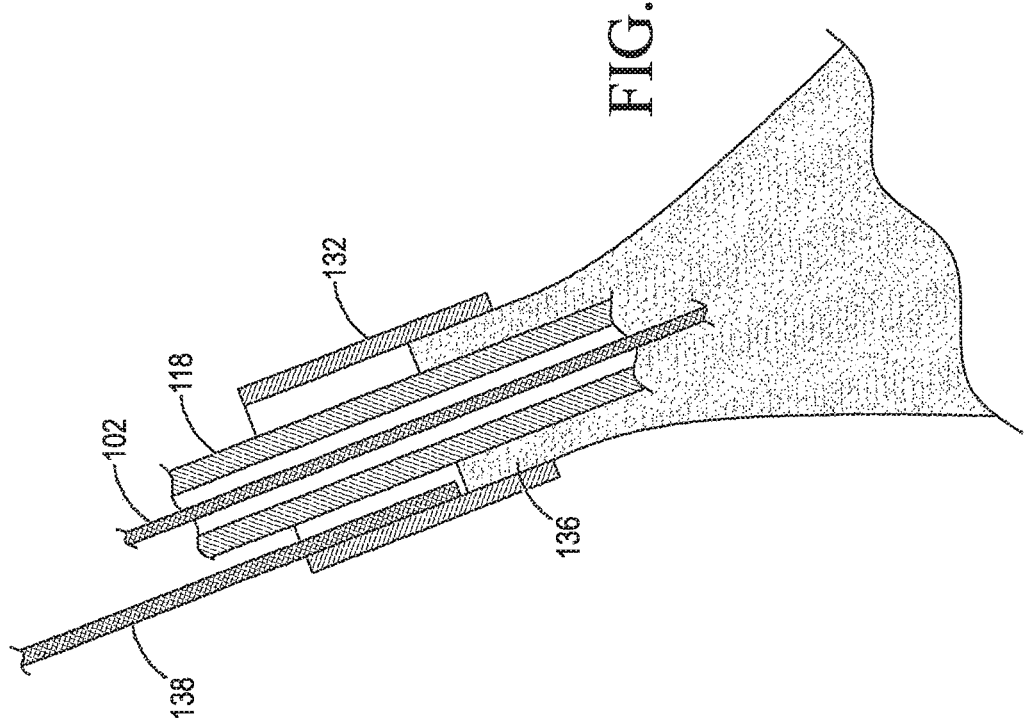
FIG. 11 is a partial cross-sectional view of the illustrative filter system of FIG. 9, taken at line 11-11.
Figure 10:
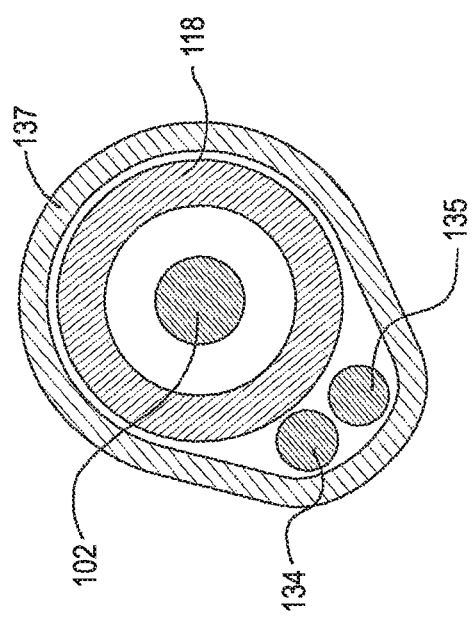
FIG. 10 is a cross-sectional view of the illustrative filter system of FIG. 9, taken at line 10-10.

FIG. 9 illustrates another alternative embodiment for the system of FIGS. 1-8. In the system 100', the handle 105 may include at least three controls (which may be sliding controls) including a control for translation of the inner member 118 relative to the handle 105, a control for translation of the delivery catheter 110 relative to the handle 105 to allow for deployment and retrieval of the filter assemblies 112, 124, and a control for deflection of the distal tip of the delivery catheter 110. In the system 100', the proximal filter bag termination 136 is connected to the proximal bond tube 132. The delivery wire 138 is also connected to the proximal bond tube 132 and the handle 105, as can be seen in FIG. 11 which is a partial cross-sectional view of the system 100' taken at line 11-11 of FIG. 9. Thus, movement of the handle 105 is translated to the proximal bond tube 132. However, in the embodiment of FIG. 9, the proximal end 130 of the aortic ring 126 is connected to the inner member 118 via the aortic ring connectors 134, 135. For example, referring to FIG. 10, which is a partial cross-sectional view of the system 100' taken at line 10-10 of FIG. 9, the aortic ring connectors 134, 135 may be coupled to the inner member 118 via a connection tube 137, which may be a heat shrink tube. The distal end 139 of the aortic ring 126 may be coupled to the distal filter frame 114 via a distal support strut 142. Thus, the aortic ring 126, the distal filter frame 114, the distal filter membrane 120, and the inner member 118 may all be advanced and retracted relative to the delivery catheter or outer sheath 110 with the first control element 111 in the handle 105. The steerable delivery catheter 110 may be withdrawn relative to the handle 105 to deploy the devices 112, 124 using a second handle control 107. The tip of the delivery catheter 110 may be deflected to assist with cannulation of the left subclavian artery 16 (or the brachiocephalic artery 12) using a third handle control (not explicitly shown).

Figure 12:
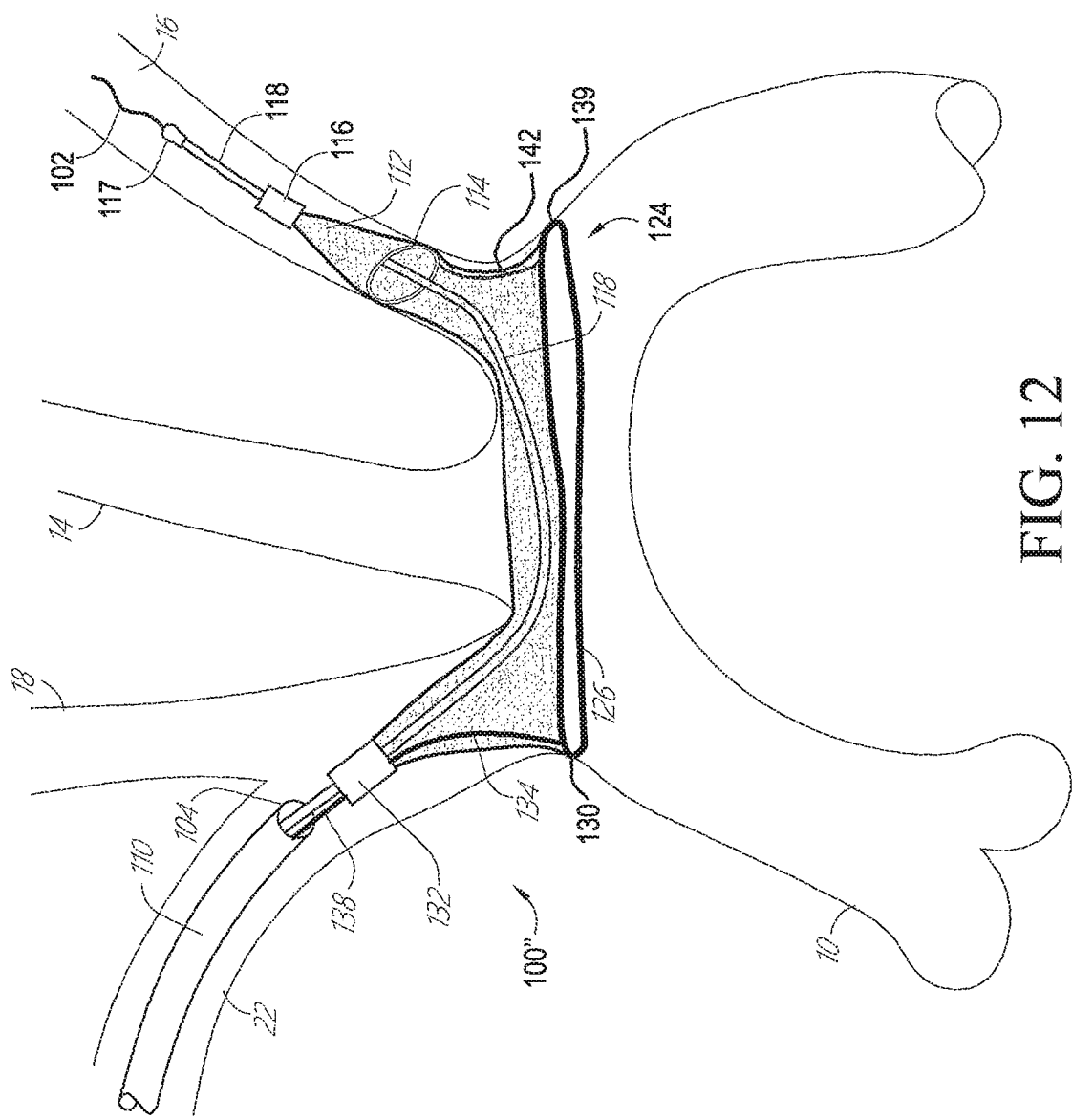
FIG. 12 illustrates another alternative embodiment a filter system.

FIG. 12 illustrates another alternative embodiment for the system of FIGS. 1-8. In the illustrative system 100'' of FIG. 12, the handle 105 may include at least three controls (which may be sliding controls) including a control for translation of the inner member 118 relative to the handle 105, a control for translation of the delivery catheter 110 relative to the handle 105 to allow for deployment and retrieval of the filter assemblies 112, 124, and a control for deflection of the distal tip of the delivery catheter 110. The proximal filter bag termination 136 is connected to the proximal bond tube 132. The delivery wire 138 and the aortic ring connector 134 are also connected to the proximal bond tube 132 and the handle 105. Thus, movement of the handle 105 is translated to the proximal bond tube 132. In the embodiment of FIG. 12, the distal end 139 of the aortic ring 126 may be coupled to the distal filter frame 114 via a distal support strut 142. Thus, the proximal filter bag termination 136, the aortic ring 126 and the distal filter frame 114 are all fixed relative to the handle 105. In other words, movement of the handle 105 is translated to the proximal bond tube 132 via the delivery wire 138 and as the aortic ring 126 is coupled to the proximal bond tube 132 and the distal filter frame, the aortic ring 126 and the distal filter frame 114 also move with the handle 105. The distal filter bag termination 116 is connected to the inner member 118 and is advanced and retracted relative to the delivery catheter 110 with a first handle control 111 (e.g., via movement of the inner member 118). The steerable delivery catheter 110 may be withdrawn relative to the handle 105 to deploy the device using a second handle control 107. The tip of the delivery catheter 110 may be deflected to assist with cannulation of the left subclavian artery 16 (or the brachiocephalic artery 12) using a third handle control (not explicitly shown).

Figure 13:
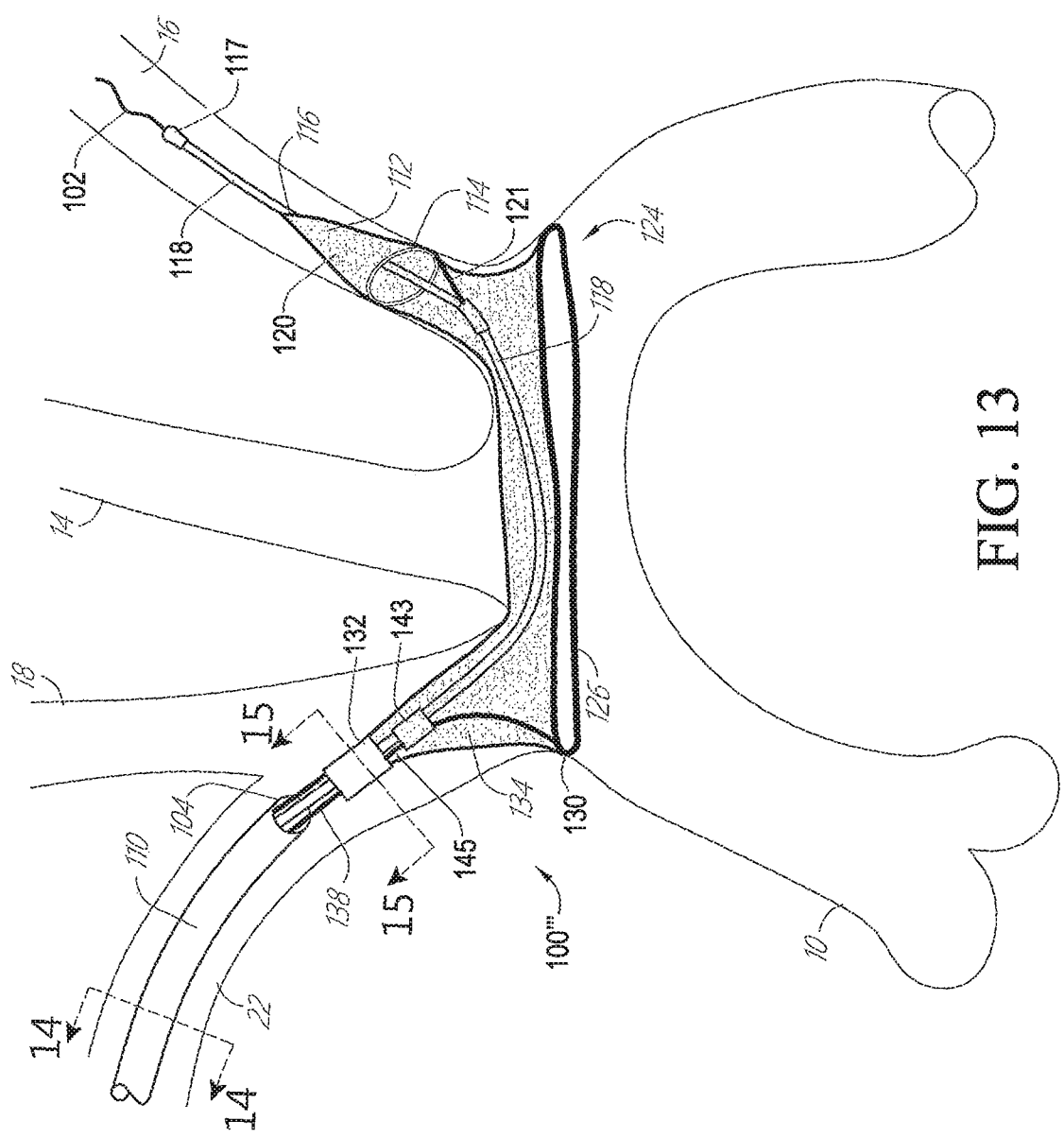
FIG. 13 illustrates another alternative embodiment a filter system.

FIG. 13 illustrates another alternative embodiment for the system of FIGS. 1-8. In the illustrative system 100''' of FIG. 13, the proximal filter bag termination 136 is connected to a first proximal bond tube 132 and is fixed relative to the handle 105 via the deployment wire 138 which is also coupled to the first proximal bond tube 132 and the handle 105. The distal filter frame 114, and thus the distal filter bag termination 116, are connected to the inner member 118. Both the distal filter frame 114 and the distal filter bag termination 116 are advanced and retracted relative to the delivery catheter 110 with a first handle control 111. The steerable delivery catheter 110 may be withdrawn relative to the handle 105 to deploy the device 112, 124 using a second handle control 107. The tip of the delivery catheter 110 may be deflected to assist with cannulation of the left subclavian artery 16 (or the brachiocephalic artery 12) using a third handle control (not explicitly shown). The proximal end 130 of the aortic ring 126 is connected to a sliding aortic ring bond tube 143 via the aortic ring connector 134. The second sliding bond tube 143 is also coupled to an aortic ring deployment wire 145. The second sliding bond tube 143 may be advanced and retracted relative to the delivery catheter 110 with a fourth handle control (not explicitly shown).

The handle 105 of the system 100''' may include at least four controls (which may be sliding controls) including a control for translation of the inner member 118 relative to the handle 105, a control for translation of the delivery catheter 110 relative to the handle 105 to allow for deployment and retrieval of the filter assemblies 112, 124, a control for deflection of the distal tip of the delivery catheter 110, and a control for translation of the aortic ring deployment wire 145 relative to handle 105. This may allow the aortic ring connector 134 (and thus the aortic ring 126), the inner member 118 and the proximal bond tube 132 (and thus the proximal filter membrane 128) to all be adjusted relative to each other. This may allow the apposition of the aortic ring 126 to the roof of the aortic arch 10 to be further optimized. In one technique, the position of the aortic ring connector 134 may be fixed, and the position of the proximal bond tube 132 (and thus the proximal termination of the filter membrane 136), to be withdrawn towards the handle 105. This applied tension on the proximal membrane 128 may draw the aortic ring 126 towards the roof or the aortic arch 10, and increase the bend in the aortic ring connector 134, thus improving apposition between the aortic ring 126 and the roof of the aortic arch 10.

FIG. 14 illustrates a cross-sectional view of the illustrative system 100''', taken at line 14-14 of FIG. 13. In the illustrated embodiment, the sidewall of delivery catheter or outer sheath 110 is provided with a pull wire lumen 144 for axially moveably receiving a pull wire 140 which may be proximally retracted to deflect the distal tip laterally. A second pull wire may alternatively be provided, such as at 180 degrees around the catheter 110 from the first pull wire, to facilitate straightening or deflecting the catheter in a second, opposite direction. Further, in some embodiments, the outer sheath 110 may include a reinforcement braid 131, although this is not required. The deployment wire 138 and the aortic ring deployment wire 145 may extend within the lumen of the outer sheath 110 but exterior to the inner member 118.

FIG. 15 is a cross-sectional view of the illustrative system 100''' taken at line 15-15 of FIG. 13. As can be seen, the proximal bond tube 132 defines a lumen 133. The inner member 118 may be slidably disposed within the lumen 133 such that the inner member 118 is separately movable from the proximal bond tube 132. Further, the aortic ring deployment wire 145 may also extend through the lumen 133 such that the aortic ring deployment wire 145 (and thus the second bond tube 143) is separately movable from the proximal bond tube 132. The proximal filter bag termination 136 may be coupled to an inner surface of the proximal body 132. However, other coupling configurations can be used, as desired. Further, the deployment or control wire 138 may also be coupled to the proximal bond tube 132. The control wire 138 may be coupled directly to the proximal bond or indirectly coupled (e.g., with the proximal filter bag termination 136 disposed therebetween), as desired. Both the proximal bond tube 132 and the aortic ring bond tube 143 may slide freely over (and/or relative to) the inner member 118.

In the protection systems 100, 100', 100'', 100''' it may be desirable for correct deployment, functioning and retrieval of the filter assemblies 112, 124 for the rotational orientation between the delivery catheter 110, the proximal bond tube 132, and the inner member 118 to be controlled. Control of the inner member 118 (and thus the distal filter assembly 112) orientation relative to the aortic ring 126 (and thus the proximal bond tube 132) may prevent the distal filter frame 114 from rotating relative to the aortic ring 126 and/or proximal bond tube 143132, and resulting in a twist in the membrane 128 between the aortic ring 126 and the distal filter assembly 112, leading to possible restriction of flow of blood and/or debris into the distal filter assembly 112 and thus the left subclavian artery. It may be desirable to control the inner member 118 (and thus the distal filter assembly 112) and the aortic ring 126 (and thus proximal bond 132) orientations relative to the delivery catheter 110, and thus to the deflection direction of the deflectable outer sheath 110, to ensure that the device 112, 124 deploys from the tip of the delivery catheter 110 in the aortic arch 10 in the correct orientation.

Figure 17:
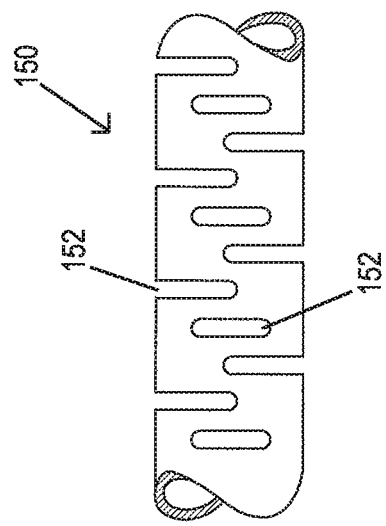
FIG. 17 is a partial side view of the illustrative deployment tube of FIG. 16.
Figure 16:
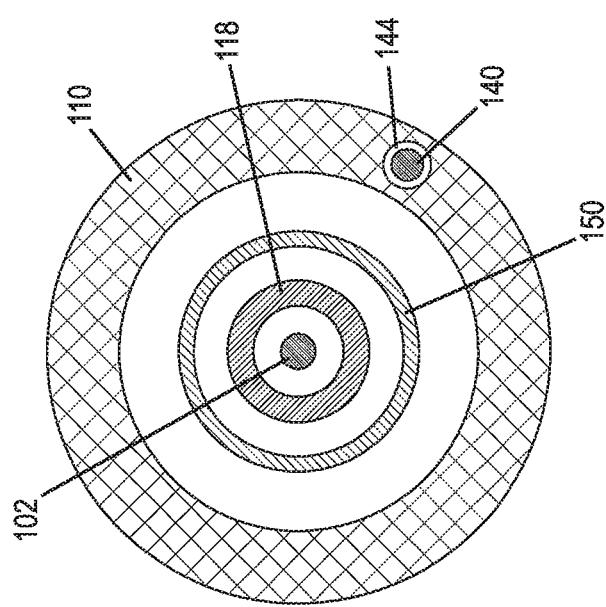
FIG. 16 is a cross-sectional view of an alternative deployment tube.

It is contemplated that the orientation may be controlled by fixing the rotational orientation of the deployment wire 138 (and thus the proximal bond tube 132) relative to the inner member 118 at the attachment points within the handle 105. If the orientation of the deployment wire 138 and the inner member 118, where they are attached to the handle 105, are fixed, the orientation of the proximal bond tube 132 and the distal filter assembly 112 may be controlled. However, the handle 105 may be separated from the distal filter assembly 112 by some distance, and the connecting inner member 118 and deployment wire 138 may twist or torque relative to each other resulting in a misalignment of the distal filter assembly 112 to the aortic ring 126. This twisting may be reduced by replacing the deployment wire 138 with a deployment tube 150 that runs in the annular space between the delivery catheter 110 and the inner member 118. FIG. 16 illustrates a cross-sectional view of this feature. Constructing the deployment wire from a tube 150 may have the advantage that a tube resists torque more effectively than a wire, and may result in better alignment between the proximal bond tube 132 and the aortic ring 126 as the tube structure 150 may rotationally deflect to a lesser degree than the wire. The tube 150 may be constructed of polymer, braid reinforced polymer, stainless steel or other metal. FIG. 17 illustrates a partial side view of an illustrative delivery tube 150 constructed of stainless steel, nitinol or other metal hypo tube with laser cut slots 152 to improve flexibility while maintaining axial and torsional stiffness to maintain the position (axially and rotationally) of the proximal bond tube 132 relative to the handle 105.

Figure 18:
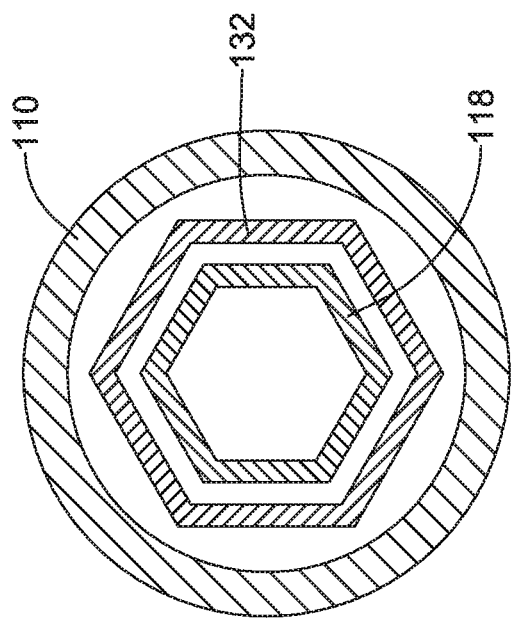
FIG. 18 is a cross-sectional view of an alternative inner member keying system.

In another illustrative embodiment, the orientation may be controlled by keying the proximal bond tube 132 to the inner member 118 such that the proximal bond tube 132 can slide freely over the inner member 118, but cannot rotate relative to the inner member 118. For example, orientation of the proximal bond tube 132 relative to the inner member 118 may be controlled at the proximal bond tube 132 instead of, or in addition to, at the handle 105. This may be done by creating a non-round or non-circular profile (e.g., a non-circular cross-sectional shape) of the inner member 118 in at least the region where the proximal bond tube 132 slides over the inner member 118. This profile (e.g., cross-sectional shape) could be square, hexagonal, triangular, or other non-round profiles. The inner opening of the proximal bond tube 132 may be profiled or keyed to match the cross-section of the inner member 118 such that it can slide along the inner member 118, but not rotate relative to the inner member 118. FIG. 18 illustrates a cross-sectional view of such a keyed arrangement between the inner member 118 and at least a portion of the proximal bond tube 132. While not explicitly shown, when so provided, the aortic ring bond tube 143 and the inner member 118 may be similarly keyed. In some cases, the proximal bond tube 132 may have a circular outer profile while the shape of the lumen is keyed or shaped to match a shape of an outer surface of the inner member 118 to limit rotation of the inner member 118.

The inner member 118 may be constructed of a polymer, a metal, a composite, a wire, a braid reinforced polymer such as polyimide, nylon, Pebax, etc., or other suitable material. The inner member 118 may be constructed with variable stiffness so that, for example, the distal portion is less stiff than the proximal portion. However, this is not required. In some embodiments, limit stops may be added to the inner member 118 to limit travel of the aortic ring connector 134, 135 (and thus the aortic ring 126) relative to the inner member 118, in both the proximal and distal directions. The inner member 118 may moves freely through the proximal bond tube 132. The limit stops may prevent the operator from extending the inner member 118 to the extent that the inner member 118 would protrude out of the aortic ring 126 and/or prevent the operator from withdrawing the inner member 118 to the extent that the distal filter assembly 112 is pulled out of correct placement in the left subclavian artery 16. By placing hard stops (e.g., structural features extending from an outer surface of the inner member 118) on the inner member 118 on either side of the proximal bond tube 132, the distance that an operator can pull or push on the inner member 118 can be controlled.

The proximal end 136 of the proximal filter membrane 128 may be terminated at the proximal bond tube 132. Apposition and sealing of the proximal filter membrane 128 in the brachiocephalic artery 12 may be achieved through a combination of sealing of the aortic ring 126 to the roof of the aortic arch 10, and the expansion of the filter membrane 128 against the walls of the brachiocephalic artery 12 due to blood flow through the filter membrane 128. In alternate embodiments, a proximal filter frame (e.g., similar in form and function to the distal filter frame 114) may be added to ensure that the filter membrane 128 opens fully in the brachiocephalic artery 12. This proximal filter frame may be constructed to provide positive circumferential contact between the membrane 128 and the walls of the brachiocephalic artery 12 or may function to ensure that the filter is open yet not circumferentially press the membrane 128 against the vessel walls. As with the distal filter frame 114, the proximal filter frame may be bonded to the membrane or may freely float inside the membrane.

In some embodiments, the self-expanding distal filter frame 114 may alternately not be bonded to the filter membrane 120 so that the distal filter frame 114 may rotate relative to the membrane 120 to prevent twisting of the membrane but would still act to hold the membrane 120 open inside the left subclavian artery 16 (or the brachiocephalic artery 12). The inner member 118 may be extended past distal filter assembly 112 to stabilize distal filter assembly 112. Also, the guidewire 102 may be extended beyond the distal filter assembly 112 to stabilize the distal filter assembly 112 in the left subclavian artery 16 and help maintain apposition of the filter frame to the vessel wall.

The distal filter assembly 112 is anchored in the left subclavian artery 16 by the expansion of the distal filter frame 114 to stabilize the device during delivery of the proximal filter assembly 124. Alternatively, or additionally, this anchoring function could be performed by an expanding anchor element that is inside of or distal to the filter membrane 120. This could take the form of a self-expanding stent structure, expanding coil, inflatable balloon, etc. This feature may be helpful holding the position of the filter assembly 112 and thus the distal portion of the device when the inner member 118 is tensioned.

Figure 19:
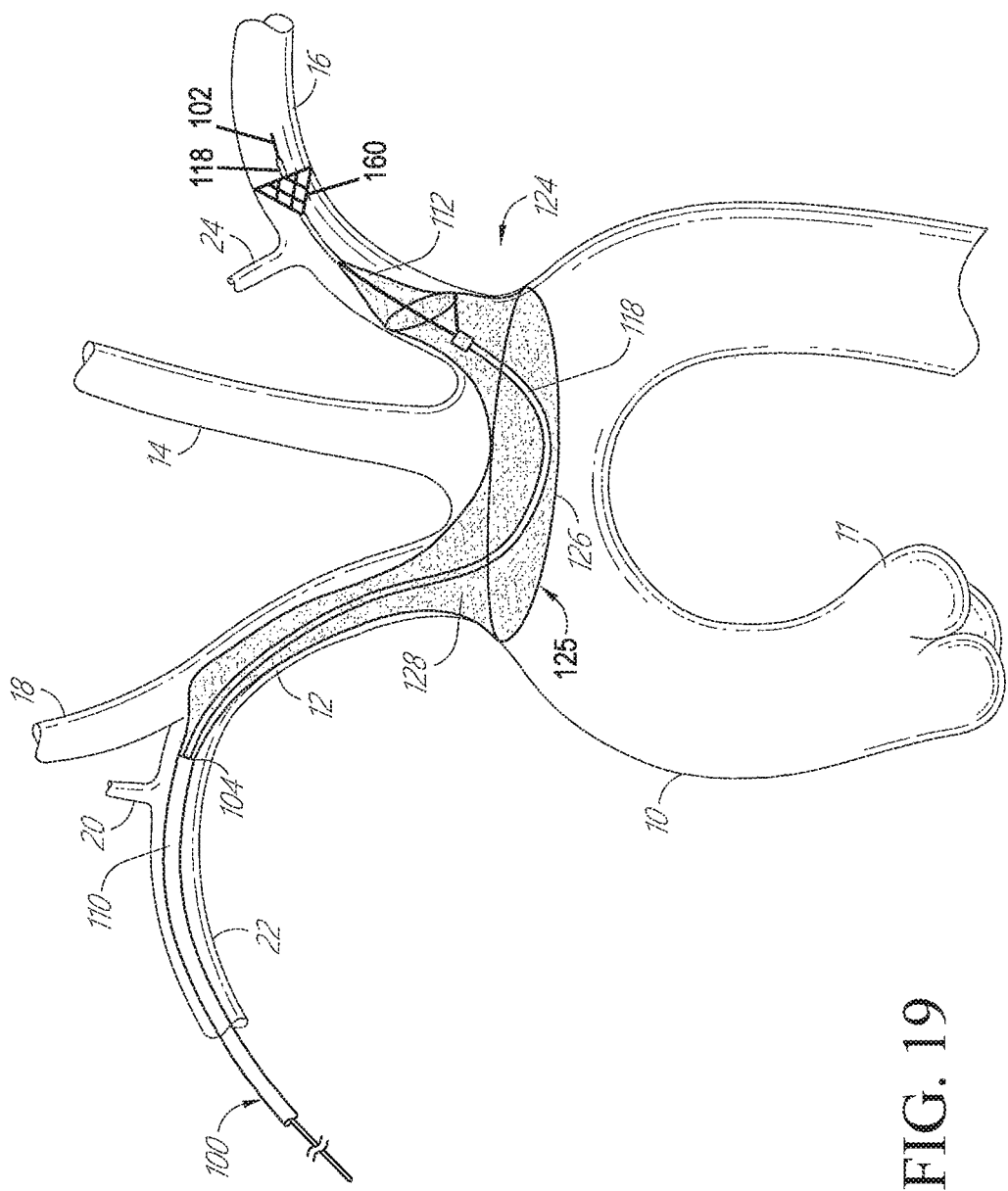
FIGS. 19-21 illustrate alternative distal anchoring mechanisms.

FIG. 19 is a first illustrative alternative distal anchoring structure 160 positioned distal to the distal filter assembly 112. A self-expanding nitinol mesh anchor 160 or similar component to help hold the position of the distal end of the device. This nitinol mesh 160 can be located between the distal filter assembly 112 and the tip or at the very tip of the catheter. The mesh anchor structure 160 can also be of any shape including but not limited to conical, cylindrical, etc.

Figure 20:
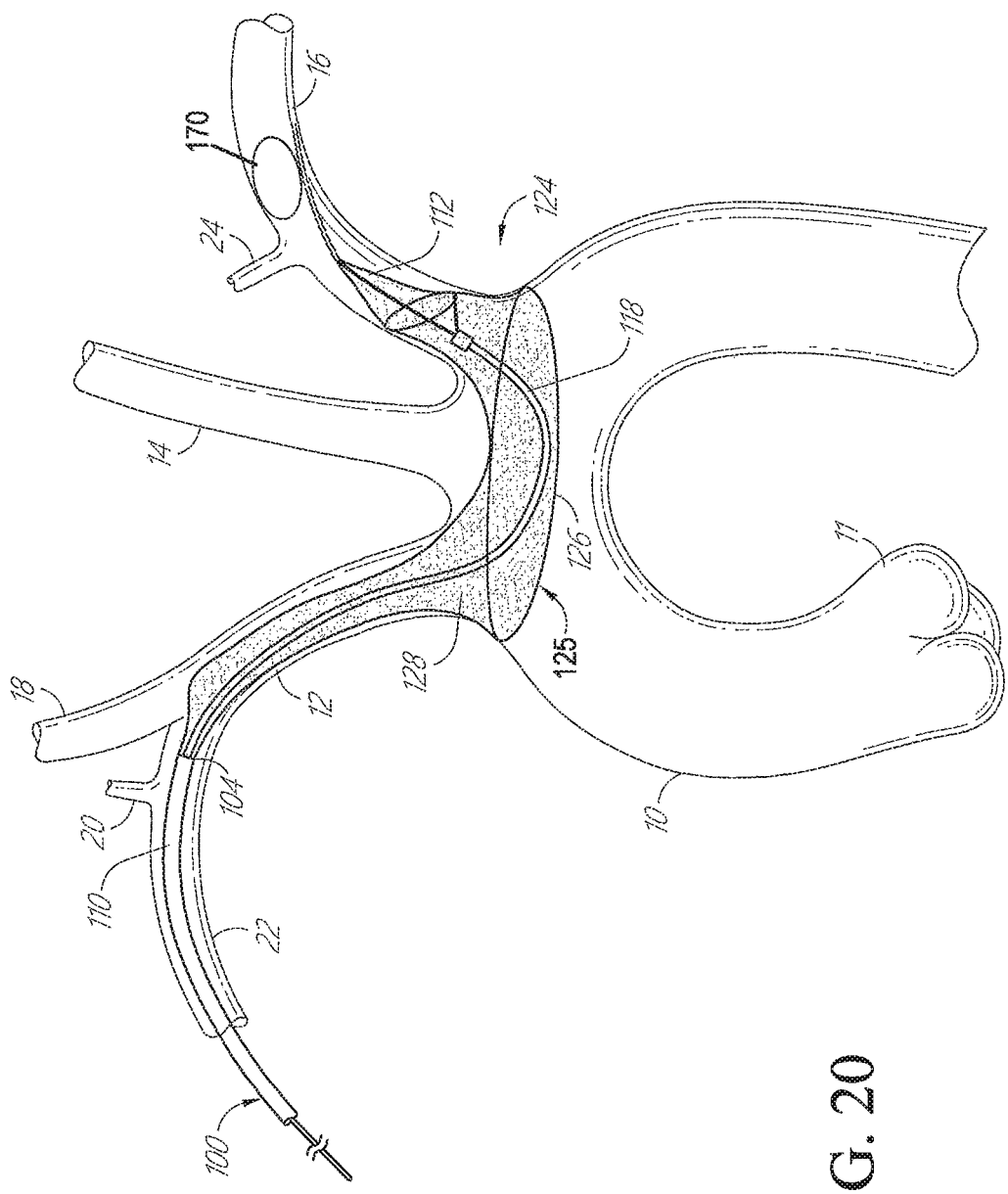

FIG. 20 illustrates another alternative distal anchoring structure including an expandable balloon 170 positioned distal to the distal filter assembly 112. In some cases, the expandable balloon 170 may be located on one side of the inner member 118 distal to the distal filter assembly 112. When in position, the balloon 170 can be expanded to help hold the position of the distal end of the inner member 118. Placing the balloon 170 on one side of the inner member 118 may allow blood flow to continue along the other sides of the inner member 118.

Figure 21:
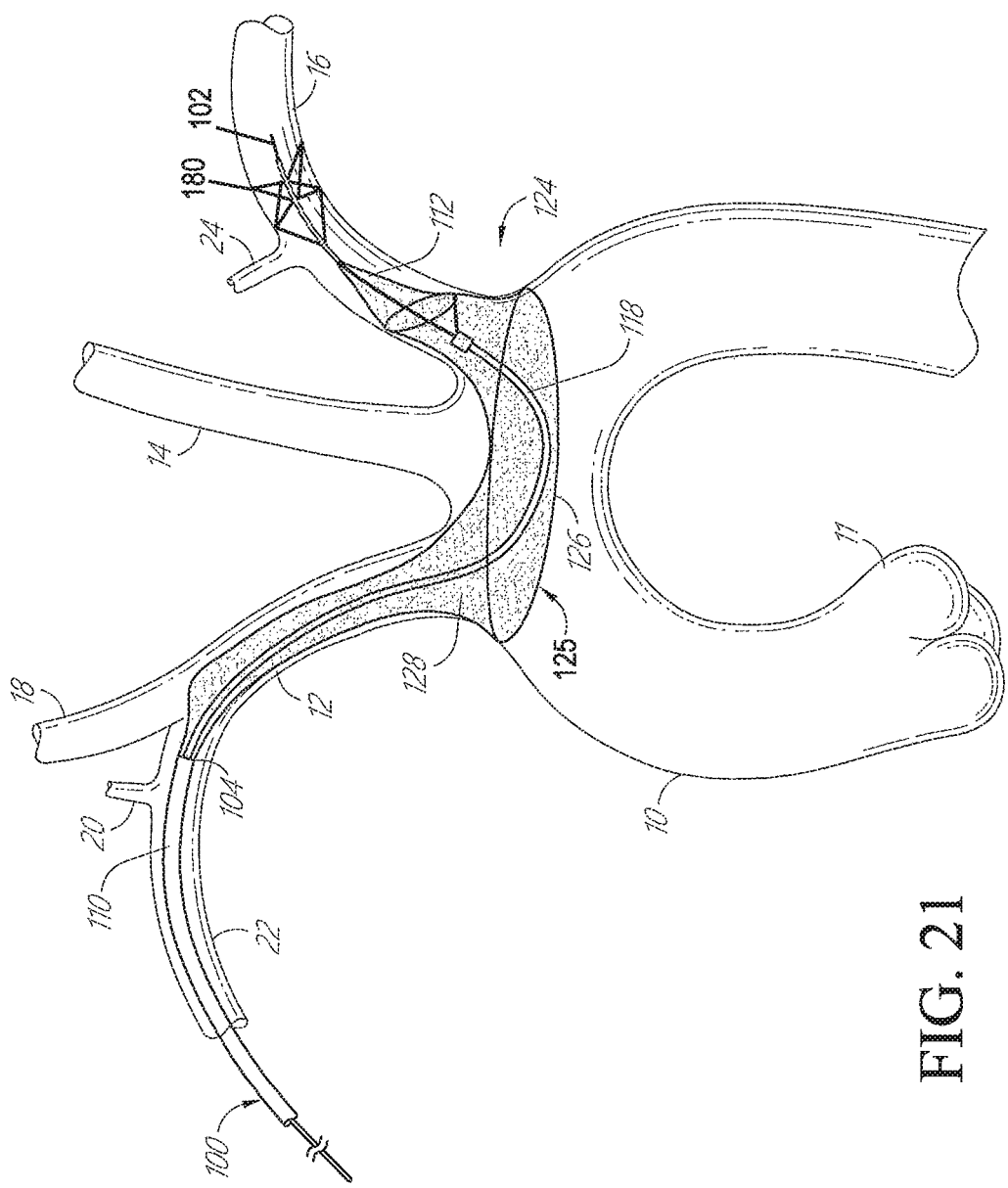

FIG. 21 illustrates another alternative distal anchoring structure including one or more nitinol rings 180 that can expand after the outer sheath 110 is withdrawn. These nitinol rings 180 can then help anchor the distal end of the inner member 118 in the left subclavian artery 16.

The filter membranes 120, 128 may be constructed of laser drilled or perforated polymer membrane, woven nitinol wire mesh, other metal mesh, woven PEEK or other polymer mesh, etc. The porosity of the filter membranes 120, 128 may be around 140 microns, however other porosities, either larger or smaller, are possible. The membrane hole pattern may be uniform, or the membrane may be perforated selectively in given regions of the membrane 120, 128 to either allow or restrict flow in those select regions to improve flow through lumens, encourage apposition, etc. The filter membrane 120, 128 may have fabric or other reinforcing or stiffening in selected areas to improve sheathing, unsheathing, folding of the membrane and apposition performance, see For example, the proximal filter membrane 128 may include is a strip of fabric reinforcement in the membrane material that extends from the point where the aortic ring connector 134 meets the aortic ring 126 to the proximal bond tube 132. The fabric reinforcement may prevent or reduce bunching of the membrane 128 during resheathing, and may help the membrane 128 fold in a controlled manner during sheathing.

The aortic ring 126 and/or the distal filter frame 114 may be constructed of nitinol wire, as described herein, however they may constructed with other flexible materials such as polymer, stainless steel, a composite of multiple material, woven or braided like a cable, etc. The aortic ring 126 and/or the distal filter frame 114 may also be laser cut from a flat sheet of metal, polymer, etc. and then formed or shape set to the desired final shape.

The aortic ring 126 may be constructed such that it is stiffer or more flexible in some section than in other. For example, if the aortic ring 126 is constructed of nitinol wire, it may be selectively ground to reduce the diameter or thickness to alter stiffness to improve performance, improve apposition, make sheathing easier, etc.

Radiopaque markers may be added to the filter frame(s) 114, the aortic ring 126, the aortic ring connectors 134, 135 and/or other portions of the device to allow visualization under fluoroscopy. The marker may be placed in selective locations or may be in the form of a coil placed over the entire aortic ring 126, filter hoop 114 or connector structures 134, 135 as needed to help with positioning and visualization.

The aortic connector 134, 135 may be constructed of more rigid materials such as nitinol, stainless steel, polymer, etc., or may be constructed of more flexible materials such as suture, fabric, or other flexible material that will still support tension to allow sheathing of the aortic ring but would allow improved apposition of aortic ring to the roof of the aorta. The aortic ring 126 may be constructed from a loop of material, for example nitinol wire, and thus the aortic ring connector 134, 135 may be formed by the two ends of the loop, and then terminated at the proximal bond tube 132. The mechanical characteristics of the aortic ring connector 134, 135 may be altered by many methods including the addition of heat shrink 190 over the wires 134, 135, as illustrated in FIG. 22A, the addition of a stiffening ribbon 192 (with or without a heat shrink layer 190), as shown illustrated in FIG. 22B, or using multiple layers of polymer. 190, 194 (with or without a stiffening ribbon 192), as illustrated in FIG. 22C The aortic ring connector(s) 134, 135 may be curved or shaped to improve aortic ring apposition on the proximal edge of the brachiocephalic 12 or left subclavian 16 artery ostia. The aortic ring connector may be formed in a curved shape (as opposed to a straight connector) may allow the aortic ring 126 to fully cover the brachiocephalic artery 12 without leaving a gap on the proximal edge 130.

Figure 23:
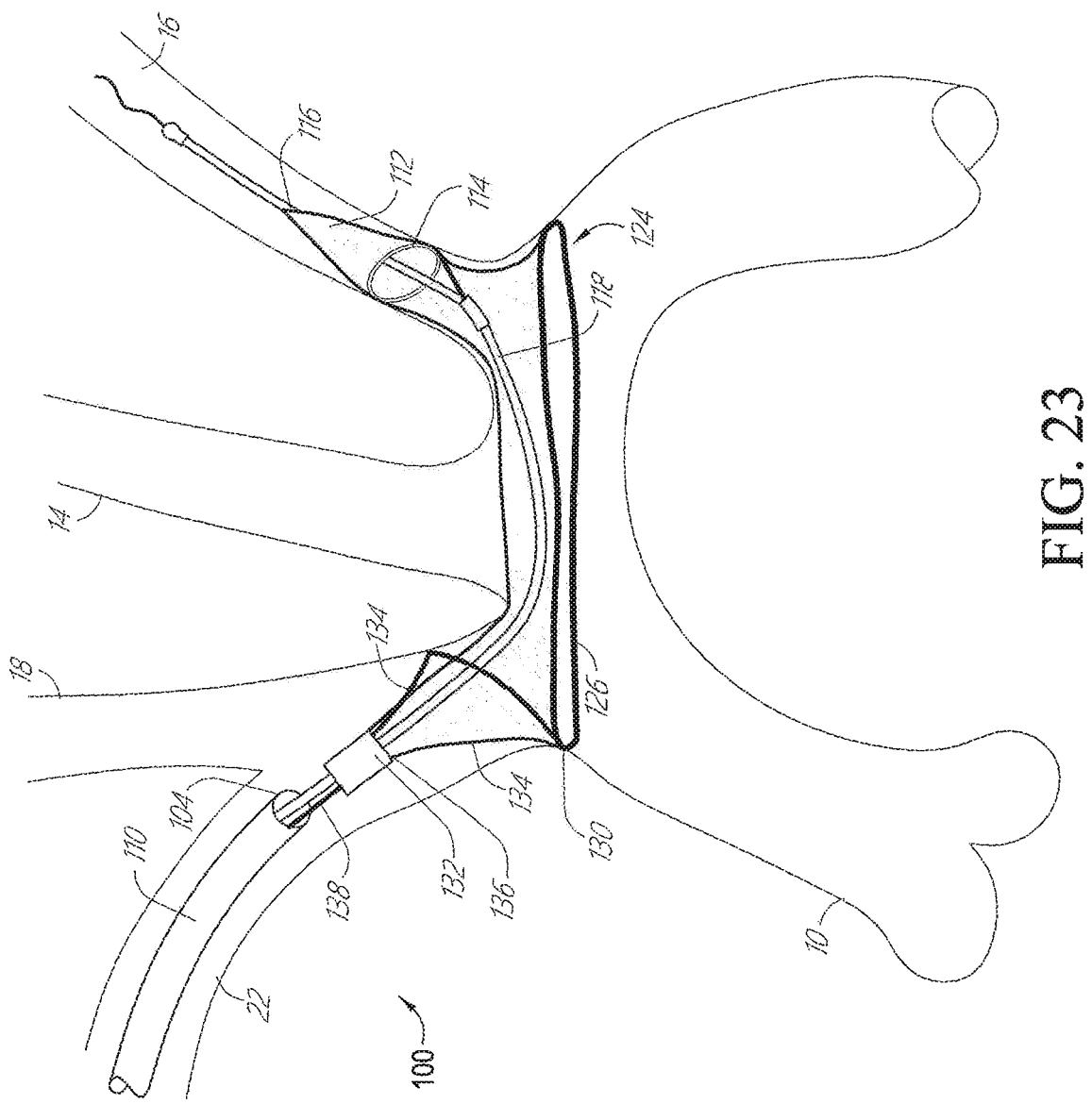
FIG. 23 illustrates an alternative aortic ring connector configuration.

In some embodiments, the aortic ring connector 134, 135 may improve apposition of the aortic ring 126 to the roof of the aortic arch 10 by for including a back-bend shape FIG. 23 illustrates an aortic ring connector 134 including curved shape that bends back on itself. In addition, the shape and bend of the aortic ring connector 134 may be adjustable. For example, the aortic ring connector 134 may include an adjustable tension member to allow the apposition of the aortic ring 126 to the roof of the aortic arch to be adjusting and optimized following deployment.

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing certain embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages. The methods disclosed herein may include certain actions taken by a practitioner; however, the methods can also include any third-party instruction of those actions, either expressly or by implication. For example, actions such as "deploying a self-expanding filter" include "instructing deployment of a self-expanding filter." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 7 mm" includes "7 mm." Phrases preceded by a term such as "substantially" include the recited phrase and should be interpreted based on the circumstances (e.g., as much as reasonably possible under the circumstances). For example, "substantially straight" includes "straight."

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed:

1. An embolic protection system for isolating the cerebral vasculature, the system comprising:
    an elongate outer sheath, having a proximal end and a distal end;
    an inner member extending through a lumen of the outer sheath;
    a distal anchoring mechanism coupled to a distal end region of the inner member, the distal anchoring mechanism comprising a self-expanding frame;
    a distal filter membrane coupled to the self-expanding frame;
    a proximal filter membrane carried between the inner member and the outer sheath, the proximal filter membrane configured to extend from the left subclavian artery to the brachiocephalic artery;
    further comprising a proximal bond tube coupled to a proximal filter bag termination of the proximal filter membrane;
    an aortic support hoop coupled to the proximal filter membrane and configured to seal the proximal filter membrane against the wall of the aorta; and
    a handle including a first actuation mechanism coupled to a proximal end of the inner member and a second actuation mechanism coupled to the proximal end of the outer sheath.

2. The embolic protection system of claim 1, wherein the inner member is slidably disposed within a lumen of the proximal bond tube.

3. The embolic protection system of claim 2, wherein a cross-sectional shape of the inner member adjacent to the proximal bond tube is non-circular and at least a portion of the proximal bond tube has a non-circular cross-sectional shape.

4. The embolic protection system of claim 1, further comprising a distal support strut extending between a distal end of the aortic support hoop and the self-expanding frame of the distal anchoring mechanism.

5. The embolic protection system of claim 1, wherein a distal end region of the outer sheath is deflectable.

6. An embolic protection system for isolating the cerebral vasculature, the system comprising:
    an elongate outer sheath, having a proximal end and a distal end;
    an inner member extending through a lumen of the outer sheath;
    a distal anchoring mechanism coupled to a distal end region of the inner member;
    a proximal filter membrane carried between the inner member and the outer sheath, the proximal filter membrane configured to extend from the left subclavian artery to the brachiocephalic artery;
    a proximal bond tube coupled to a proximal filter bag termination of the proximal filter membrane;
    an aortic support hoop coupled to the proximal filter membrane and configured to seal the proximal filter membrane against the wall of the aorta;
    a handle including a first actuation mechanism coupled to a proximal end of the inner member and a second actuation mechanism coupled to the proximal end of the outer sheath; and
    an aortic support hoop connector extending from a proximal end of the aortic support hoop to the proximal bond tube.

7. The embolic protection system of claim 6, further comprising a delivery wire coupled to the proximal bond tube and extending proximally to the handle.

8. The embolic protection system of claim 7, wherein the handle further comprises a third actuation mechanism coupled to a proximal end of the delivery wire.

9. An embolic protection system for isolating the cerebral vasculature, the system comprising:
    an elongate outer sheath, having a proximal end and a distal end;
    an inner member extending through a lumen of the outer sheath;

a distal filter assembly coupled to a distal end region of the inner member, the distal filter assembly including a self-expanding frame and a distal filter membrane coupled to the self-expanding frame;

a proximal filter membrane carried between the inner member and the outer sheath, the proximal filter membrane configured to extend from the left subclavian artery to the brachiocephalic artery;

an aortic support hoop coupled to the proximal filter membrane and configured to seal the proximal filter membrane against the wall of the aorta;

a proximal bond tube coupled to a proximal filter bag termination of the proximal filter membrane;

an aortic support hoop connector coupled to and extending between a proximal end of the aortic support hoop and the proximal bond tube;

a delivery wire coupled to and extending proximally from the proximal bond tube; and a handle including a first actuation mechanism coupled to a proximal end of the inner member, a second actuation mechanism coupled to the proximal end of the outer sheath, and a third actuation mechanism coupled to a proximal end of the delivery wire.

10. The embolic protection system of claim 9, further comprising a distal anchoring structure positioned distal to the distal filter assembly.

11. The embolic protection system of claim 9, wherein the aortic support hoop connector includes a curved shape.

* * * * *